US011096962B2

(12) United States Patent
Marill et al.

(10) Patent No.: US 11,096,962 B2
(45) Date of Patent: Aug. 24, 2021

(54) NANOPARTICLES FOR USE AS A THERAPEUTIC VACCINE

(71) Applicant: NANOBIOTIX, Paris (FR)

(72) Inventors: Julie Marill, Le Perreux sur Marne (FR); Agnes Pottier, Paris (FR); Laurent Levy, Paris (FR)

(73) Assignee: NANOBIOTIX, Paris (FR)

( * ) Notice: Subject to any disclaimer, the term of this patent is extended or adjusted under 35 U.S.C. 154(b) by 0 days.

(21) Appl. No.: 15/577,482

(22) PCT Filed: May 27, 2016

(86) PCT No.: PCT/EP2016/061989
§ 371 (c)(1),
(2) Date: Nov. 28, 2017

(87) PCT Pub. No.: WO2016/189125
PCT Pub. Date: Dec. 1, 2016

(65) Prior Publication Data
US 2018/0147237 A1 May 31, 2018

(30) Foreign Application Priority Data
May 28, 2015 (EP) .................................... 15305810

(51) Int. Cl.
A61K 33/24 (2019.01)
A61K 38/19 (2006.01)
A61K 41/00 (2020.01)
A61K 9/51 (2006.01)
A61K 9/00 (2006.01)
A61P 35/04 (2006.01)
A61N 5/10 (2006.01)
A61K 33/242 (2019.01)
A61K 45/06 (2006.01)
A61K 39/00 (2006.01)
A61K 33/243 (2019.01)

(52) U.S. Cl.
CPC .......... A61K 33/242 (2019.01); A61K 9/0009 (2013.01); A61K 9/5115 (2013.01); A61K 33/243 (2019.01); A61K 38/19 (2013.01); A61K 39/0011 (2013.01); A61K 41/0038 (2013.01); A61K 45/06 (2013.01); A61P 35/04 (2018.01); A61K 2039/55555 (2013.01); A61K 2039/70 (2013.01); A61N 2005/1098 (2013.01)

(58) Field of Classification Search
CPC combination set(s) only.
See application file for complete search history.

(56) References Cited

U.S. PATENT DOCUMENTS

| 4,280,918 | A | 7/1981 | Homola et al. |
| 4,672,040 | A | 6/1987 | Josephson |
| 4,770,183 | A | 9/1988 | Groman et al. |
| 5,225,212 | A | 7/1993 | Martin et al. |
| 5,370,901 | A | 12/1994 | Tournier et al. |
| 5,395,619 | A | 3/1995 | Zalipsky et al. |
| 5,582,172 | A | 12/1996 | Papisov et al. |
| 6,117,454 | A | 9/2000 | Kreuter et al. |
| 6,200,598 | B1 | 3/2001 | Needham |
| 6,251,365 | B1 | 6/2001 | Bäuerlein et al. |
| 6,514,481 | B1 | 2/2003 | Prasad et al. |
| 6,541,039 | B1 | 4/2003 | Lesniak et al. |
| 6,726,925 | B1 | 4/2004 | Needham |
| 6,955,639 | B2 | 10/2005 | Hainfeld et al. |
| 7,367,934 | B2 | 5/2008 | Hainfeld et al. |
| 7,427,393 | B2 | 9/2008 | Takeyama |
| 8,845,507 | B2 | 9/2014 | Levy et al. |
| 9,700,621 | B2 | 7/2017 | Levy et al. |
| 9,956,175 | B2 | 5/2018 | Pottier et al. |
| 2002/0061298 | A1 | 5/2002 | Coffey et al. |
| 2002/0127224 | A1 | 9/2002 | Chen |
| 2002/0155507 | A1 | 10/2002 | Bruchez et al. |
| 2002/0177583 | A1 | 11/2002 | Kiss |
| 2003/0125283 | A1 | 7/2003 | Gatenby |
| 2003/0191458 | A1 | 10/2003 | Diamond et al. |
| 2004/0014060 | A1 | 1/2004 | Hoheisel et al. |
| 2004/0181114 | A1 | 9/2004 | Hainfeld et al. |
| 2004/0208825 | A1 | 10/2004 | Carpenter et al. |
| 2004/0242953 | A1 | 12/2004 | Good |
| 2005/0084869 | A1 | 4/2005 | Kim |
| 2005/0087719 | A1 | 4/2005 | Gansau et al. |

(Continued)

FOREIGN PATENT DOCUMENTS

DE 10 2006 041495 3/2008
DE 10 2008 00852 8/2009

(Continued)

OTHER PUBLICATIONS

Bickford, L. R. et al. "Silica-gold nanoshells as potential intraoperative molecular probes for HER2-overexpression in ex vivo breast tissue using near-infrared reflectance confocal microscopy" *Breast Cancer Res Treat*, 2010, pp. 547-555, vol. 120.

Maggiorella, L. et al. "Nanoscale radiotherapy with hafnium oxide nanoparticles" *Future Oncology*, 2012, pp. 1167-1181, vol. 8, No. 9.

Unknown "Release / Nanobiotix Starts Clinical Trial with Lead Product NBTXR3" *Nanobiotix*, Sep. 13, 2011, pp. 1-2, XP-002671267.

Praetorius, N. P. et al. "Engineered Nanoparticles in Cancer Therapy" *Recent Patents on Drug Delivery & Formulation*, 2007, pp. 37-51, vol. 1.

Written Opinion in International Application No. PCT/EP2016/061989, dated Jul. 27, 2016, pp. 1-6.

Zhang, X.-D. et al. "Size-dependent radiosensitization of PEG-coated gold nanoparticles for cancer radiation therapy" *Biomaterials*, 2012, pp. 6408-6419, vol. 33.

(Continued)

Primary Examiner — Zohreh A Fay
(74) Attorney, Agent, or Firm — Saliwanchik, Lloyd & Eisenschenk

(57) ABSTRACT

The present invention relates to the field of human health and more particularly concerns nanoparticles for use as a therapeutic vaccine in the context of radiotherapy in a subject suffering of a cancer, in particular of a metastatic cancer or of a liquid cancer.

30 Claims, 8 Drawing Sheets

(56) References Cited

U.S. PATENT DOCUMENTS

| | | |
|---|---|---|
| 2005/0090732 A1 | 4/2005 | Ivkov et al. |
| 2005/0256360 A1 | 11/2005 | Hainfeld et al. |
| 2005/0260137 A1 | 11/2005 | Acar et al. |
| 2006/0099145 A1 | 5/2006 | Takeyama |
| 2006/0264804 A1 | 11/2006 | Karmon et al. |
| 2007/0031337 A1 | 2/2007 | Schulte |
| 2007/0098642 A1 | 5/2007 | Bonitatebus, Jr. et al. |
| 2007/0110816 A1 | 5/2007 | Jun et al. |
| 2007/0197904 A1 | 8/2007 | Viglianti et al. |
| 2007/0217996 A1 | 9/2007 | Levy et al. |
| 2007/0292353 A1 | 12/2007 | Levy et al. |
| 2008/0003183 A1 | 1/2008 | Guo |
| 2008/0171982 A1 | 7/2008 | Mehier |
| 2008/0187595 A1 | 8/2008 | Jordan et al. |
| 2008/0193372 A1 | 8/2008 | Lanza et al. |
| 2009/0004258 A1 | 1/2009 | Yang et al. |
| 2009/0092661 A1 | 4/2009 | Huang et al. |
| 2009/0130050 A1 | 5/2009 | Kanehira et al. |
| 2009/0304587 A1 | 12/2009 | Rubinstein et al. |
| 2010/0040555 A1 | 2/2010 | Levy et al. |
| 2010/0112040 A1 | 5/2010 | Basheer |
| 2010/0320402 A1 | 12/2010 | Wu et al. |
| 2011/0027375 A1 | 2/2011 | Tillement et al. |
| 2011/0052609 A1 | 3/2011 | Waldoefner et al. |
| 2011/0142936 A1 | 6/2011 | Campbell et al. |
| 2011/0213192 A1 | 9/2011 | Levy et al. |
| 2011/0223255 A1 | 9/2011 | Thiesen et al. |
| 2012/0088832 A1 | 4/2012 | Mayes et al. |
| 2012/0176016 A1 | 7/2012 | Bonitatibus et al. |
| 2012/0203050 A1 | 8/2012 | Levy et al. |
| 2013/0177523 A1 | 7/2013 | Ghandehari et al. |
| 2013/0261061 A1 | 10/2013 | Acharya et al. |
| 2014/0056813 A1 | 2/2014 | Pottier et al. |
| 2014/0112931 A1* | 4/2014 | Chardes ............... C07K 16/32 424/143.1 |
| 2014/0186447 A1 | 7/2014 | Desai |
| 2014/0213765 A1 | 7/2014 | Lee |
| 2014/0219926 A1 | 8/2014 | Cunkelman et al. |
| 2014/0227343 A1 | 8/2014 | Pottier et al. |
| 2014/0271489 A1 | 9/2014 | Grinstaff et al. |
| 2014/0335015 A1 | 11/2014 | Pottier et al. |
| 2015/0374818 A1 | 12/2015 | Borghi et al. |
| 2016/0038616 A1 | 2/2016 | Pottier et al. |
| 2016/0136303 A1 | 5/2016 | Poul et al. |
| 2016/0136304 A1 | 5/2016 | Poul et al. |
| 2016/0184225 A1 | 6/2016 | Pottier et al. |
| 2016/0310614 A1 | 10/2016 | Pottier et al. |
| 2017/0258717 A1 | 9/2017 | Germain et al. |
| 2017/0258718 A1 | 9/2017 | Meyre et al. |
| 2017/0258720 A1 | 9/2017 | Potter et al. |
| 2017/0258721 A1 | 9/2017 | Germain et al. |
| 2017/0258937 A1 | 9/2017 | Meyre et al. |

FOREIGN PATENT DOCUMENTS

| | | |
|---|---|---|
| EP | 2 000 150 | 12/2008 |
| EP | 2067485 | 6/2009 |
| EP | 2 130 553 | 12/2009 |
| EP | 2 305 310 | 4/2011 |
| EP | 2 537 530 | 12/2012 |
| FR | 2 922 106 | 4/2009 |
| GB | 2415374 | 12/2005 |
| JP | H10-120597 | 5/1998 |
| JP | 2001-527534 | 12/2001 |
| JP | 2003-517453 | 5/2003 |
| JP | 2003-522149 | 7/2003 |
| JP | 2005-273011 | 10/2005 |
| JP | 2009-067613 | 4/2009 |
| JP | 2011 509233 | 3/2011 |
| JP | 2013-514152 | 4/2013 |
| JP | 2013 534459 | 9/2013 |
| WO | WO 1993/26019 | 12/1993 |
| WO | WO 96/35415 | 11/1996 |
| WO | WO 00/45854 | 8/2000 |
| WO | WO 01/37721 A2 | 5/2003 |
| WO | WO 03/035113 | 5/2003 |
| WO | WO 03/075961 | 9/2003 |
| WO | WO 2004/067508 | 8/2004 |
| WO | WO 05/046733 | 5/2005 |
| WO | WO 2005/063305 | 7/2005 |
| WO | WO 2005/086639 | 9/2005 |
| WO | WO 2005/120590 | 12/2005 |
| WO | WO 2006/051732 | 5/2006 |
| WO | WO 2006/138268 | 12/2006 |
| WO | WO 2007/116954 | 10/2007 |
| WO | WO 2007/128066 | 11/2007 |
| WO | WO 2008/007290 | 1/2008 |
| WO | WO 2008/033031 | 3/2008 |
| WO | WO 2008/035985 | 3/2008 |
| WO | WO 2008/059419 | 5/2008 |
| WO | WO 2009/081287 | 7/2009 |
| WO | WO 2009/105774 | 8/2009 |
| WO | WO 2009/142754 | 11/2009 |
| WO | WO 2009/147214 | 12/2009 |
| WO | WO 2010/048623 | 4/2010 |
| WO | WO 2011/003999 | 1/2011 |
| WO | WO 2011/070324 | 6/2011 |
| WO | WO 2011/084465 | 7/2011 |
| WO | WO 2011/119988 | 9/2011 |
| WO | WO 2011/133228 | 10/2011 |
| WO | WO 2011/151631 | 12/2011 |
| WO | WO 2012/051220 | 4/2012 |
| WO | WO 2012/104275 | 8/2012 |
| WO | WO 2012/104277 | 8/2012 |
| WO | WO 2013/076305 | 5/2013 |
| WO | WO 2013/087920 | 6/2013 |
| WO | WO 2014/039874 | 3/2014 |
| WO | WO 2014/057432 | 4/2014 |
| WO | WO 2014/191569 | 12/2014 |
| WO | WO 2015/091888 | 6/2015 |

OTHER PUBLICATIONS

Levy, L. et al. "Nanochemistry: Synthesis and Characterization of Multifunctional Nanoclinics for Biological Applications" *Chemistry of Materials*, 2002, pp. 3715-3721, vol. 14, No. 9.

Zorov, D.B. et al. "Examining intracellular organelle function using fluorescent probes: from animalcules to quantum dots" *Circulation Research*, Aug. 6, 2004, pp. 239-252, vol. 95, No. 3.

Akerman, M. et al. "Nanocrystal Targeting in Vivo" *Proceedings of the National Academy of Sciences of USA*, Oct. 1, 2002, pp. 12617-12621, vol. 99, No. 20.

Liu, X. et al. "Preparation and characterization of amino-silane modified superparamagnetic silica nanospheres" *Journal of Magnetism and Magnetic Materials*, 2004, pp. 1-6, vol. 270, No. 1-2.

Shibata, H. et al. "Hydroxyl Radical Generation Depending on $O_2$ or $H_2O$ by a Photocatalyzed Reaction in an Aqueous Suspension of Titanium Dioxide" *Bioscience Biotechnology Biochemistry*, Dec. 1998, pp. 2306-2311, vol. 62, No. 12.

Roy, I. et al. "Ceramic-based nanoparticles entrapping water-insoluble photosensitizing anticancer drugs: A novel drug-carrier system for photodynamic therapy" *Journal of the American Chemical Society*, Jul. 2, 2003, pp. 7860-7865, vol. 125, No. 26.

Konan, Y. et al. "Encapsulation of p-THPP into nanoparticles: Cellular uptake, subcellular localization and effect of serum on photodynamic activity" *Photochemistry and Photobiology*, Jun. 2003, pp. 638-644, vol. 77, No. 6.

Roy, I. et al. "Optical tracking of organically modified silica nanoparticles as DNA carriers: A nonviral, nanomedicine approach for gene delivery" *Proceedings of the National Academy of Sciences of the United States of America*, Jan. 11, 2005, pp. 279-284, vol. 102, No. 2.

Sahoo, Y. et al. "Aqueous Ferrofluid of Magnetite Nanoparticles: Fluorescence Labeling and Magnetophoretic Control" *Journal of Physical Chemistry B*, 2005, pp. 3879-3885.

Zhou, J. et al. "Sub-cellular accumulation of magnetic nanoparticles in breast tumors and metastases" *Biomaterials*, Mar. 2006, pp. 2001-2008, vol. 27, No. 9.

(56) References Cited

OTHER PUBLICATIONS

Paunesku, T. et al. "Biology of TiO$_2$-oligonucleotide nanocomposites" *Nature Materials*, May 2003, pp. 343-346, vol. 2, No. 5.

Jeannot, V. et al. "Intracellular Accumulation of Rhodamine 110 in Single Living Cells" *The Journal of Histochemistry & Cytochemistry*, 1997, pp. 403-412, vol. 45, No. 3.

Nori, A. et al. "Intracellular targeting of polymer-bound drugs for cancer chemotherapy" *Advanced Drug Delivery Reviews*, 2005, pp. 609-636, vol. 57.

Josephson, L. et al. "High-Efficiency Intracellular Magnetic Labeling with Novel Superparamagnetic-Tat Peptide Conjugates" *Bioconjugate Chem.*, 1999, pp. 186-191, vol. 10.

Chen, Y. et al. "Nano neodymium oxide induces massive vacuolization and autophagic cell death in non-small cell lung cancer NCI-H460 cells" *Biochemical and Biophysical Research Communications*, 2005, pp. 52-60, vol. 337, XP-002495930.

Fortin, M.-A. et al. "Polyethylene glycol-covered ultra-small Gd$_2$O$_3$ nanoparticles for positive contrast 1.5 T magnetic resonance clinical scanning" *Nanotechnology*, 2007, pp. 1-9, vol. 18, XP-002495929.

Smith, B. W. et al. "Rhenium oxide nanoparticles for the targeted radiotherapy of solid tumors" *Abstracts of Papers American Chemical Society*, Aug. 2004, p. U6, vol. 228, Part 2, XP-008096435.

Tsai, Y. et al. "Novel synthesis of cerium oxide nanoparticles for free radical scavenging" *Nanomedicine*, 2007, pp. 325-332, vol. 2, No. 3, XP-008096453.

Webb, P. A. "Volume And Density Determinations for Particle Technologists" Retrieved from the Internet: URL: http://www.micromeritics.com/pdf/app_articles/density_determinations.pdf>, Feb. 2001, pp. 1-16, XP-002495931.

Written Opinion in International Application No. PCT/EP2009/056880, dated Dec. 7, 2009, pp. 1-8.

Petri-Fink, A. et al. "Development of functionalized superparamagnetic iron oxide nanoparticles for interaction with human cancer cells" *Biomaterials*, May 2005, pp. 2685-2694, vol. 26, No. 15.

Jain, T. K. et al. "Iron Oxide Nanoparticles for Sustained Delivery of Anticancer Agents" *Molecular Pharmaceutics*, May-Jun. 2005, pp. 194-205, vol. 2, No. 3.

Johannsen, M. et al. "Evaluation of Magnetic Fluid Hyperthermia in a Standard Rat Model of Prostate Cancer" *Journal of Endourology*, Jun. 2004, pp. 495-500, vol. 18, No. 5.

Chouly, C. et al. "Development of superparamagnetic nanoparticles for MRI: effect of particle size, charge and surface nature on biodistribution" *J. Microencapsul.*, 1996, pp. 245-255, vol. 13, No. 3.

Bergey, E. J. et al. "DC magnetic field induced magnetocytolysis of cancer cells targeted by LH-RH magnetic nanoparticles in vitro" *Biomed. Microdevices*, 2002, pp. 293-299, vol. 4, No. 4.

Entry for "ferromagnetic". Dictionary.com online dictionary. <http://dictionary.reference.com/browse/ferromagnetic>. Accessed Mar. 5, 2012, pp. 1-2.

"Selected ferrites," in CRC Handbook of Chemistry and Physics, 92nd Edition (Internet version 2012), W.M. Haynes, ed., CRC Press/Taylor and Francis, Boca Raton, FL. pp. 1-5.

Liu, X. M. et al. "Synthesis of maghemite sub-microspheres by simple solvothermal reduction method" *J. Solid State Chem.*, 2006, pp. 1554-1558, vol. 179.

Brun, E. et al. "Parameters governing gold nanoparticle X-ray radiosensitization of DNA in solution" *Colloids and Surfaces B: Biointerfaces*, 2009, pp. 128-134, vol. 72, No. 1.

Zhang, S. X. et al. "Quantifying tumor-selective radiation dose enhancements using gold nanoparticles: a monte carlo simulation study" *Biomedical Microdevices*, 2009, pp. 925-933, vol. 11, No. 4.

Written Opinion in International Application No. PCT/EP2010/059871, dated Aug. 5, 2010, pp. 1-7.

Hoopes, P. J. et al. "Assessment of intratumor non-antibody directed iron oxide nanoparticle hyperthermia cancer therapy and antibody directed IONP uptake in murine and human cells" *Proc SPIE Int Soc Opt Eng.*, Feb. 23, 2009, pp. 1-17.

Mahmoudi, M. et al. "Superparamagnetic iron oxide nanoparticles (SPIONs): Development, surface modification and applications in chemotherapy" *Advanced Drug Delivery Reviews*, 2011, pp. 24-46, vol. 63.

Bakandritsos, A. et al. "Synthesis and Characterization of Iron Oxide Nanoparticles Encapsulated in Lipid Membranes" *Journal of Biomedical Nanotechnology*, 2008, pp. 313-318, vol. 4.

Fortin-Ripoche, J.-P. et al. "Magnetic Targeting of Magnetoliposomes to Solid Tumors with MR Imaging Monitoring in Mice: Feasibility" *Radiology*, May 2006, pp. 415-424, vol. 239, No. 2.

Written Opinion in International Application No. PCT/EP2012/051507, dated Sep. 11, 2012, pp. 1-7.

Aime, S. et al. "Gd-Loaded Liposomes as T$_1$, Susceptibility, and CEST Agents, All in One" *Journal of the American Chemical Society*, 2007, pp. 2430-2431, vol. 129, No. 9.

Arruebo, M. et al. "Magnetic nanoparticles for drug delivery" *Nano Today*, Jun. 2007, pp. 22-32, vol. 2, No. 3.

Written Opinion in International Application No. PCT/EP2012/051510, dated Aug. 30, 2012, pp. 1-8.

Golovko, D. et al. "Accelerated stem cell labeling with ferucarbotran and protamine" *European Journal of Radiology*, 2010, pp. 640-648, vol. 20.

Sun, Y. et al. "An improved way to prepare superparamagnetic magnetite-silica core-shell nanoparticles for possible biological application" *Journal of Magnetism and Magnetic Materials*, 2005, pp. 65-70, vol. 285.

Database EMBASE Accession No. 0018572655, Hodenius, M.A.J. et al. "Synthesis, physicochemical characterization and MR relaxometry of aqueous ferrofluids" *Journal of Nanoscience and Nanotechnology*, May 2008, p. 1.

Honda, H. et al. "Study of hyperthermia for cancer using a magnetic liposome particles" *Banyu Life Science Foundation International Drug Discovery Engineering Symposium*, 2005, pp. 29-33, vol. 5.

Toagosei Group, Research Annual Report, Jan. 1, 2011, pp. 27-30, vol. 14.

Zhao, B. et al. "Nanotoxicity comparison of four amphiphilic polymeric micelles with similar hydrophilic or hydrophobic structure" *Particle and Fibre Toxicology*, 2013, pp. 1-16, vol. 10, No. 47.

Gao, Z. et al. "Diacyllipid-Polymer Micelles as Nanocarriers for Poorly Soluble Anticancer Drugs" *Nano Letters*, 2002, pp. 979-982, vol. 2, No. 9.

Cinteza, L. O. et al. "Diacyllipid Micelle-Based Nanocarrier for Magnetically Guided Delivery of Drugs in Photodynamic Therapy" *Molecular Pharmaceutics*, Feb. 14, 2006, pp. 415-423, vol. 3, No. 4.

Andreas, K. et al. "Highly efficient magnetic stem cell labeling with citrate-coated superparamagnetic iron oxide nanoparticles for MRI tracking" *Biomaterials*, 2012, pp. 4515-4525, vol. 33.

Radu, M. et al. "Exposure to Iron Oxide Nanoparticles Coated with Phospholipid-Based Polymeric Micelles Induces Biochemical and Histopathological Pulmonary Changes in Mice." *Int. J. Mol. Sci.*, 2015, pp. 29417-29435, vol. 16.

McCarthy, J. R. et al. "Multifunctional magnetic nanoparticles for targeted imaging and therapy" *Advanced Drug Delivery Reviews*, 2008, pp. 1241-1251, vol. 60.

Nanobiotix: "Release / Nanobiotix Starts Clinical Trial with Lead Product NBTXR3", Sep. 13, 2011, XP-002671267, Retrieved from Internet: URL:http://www.nanobiotix.com/news/release/nanobiotix-starts-clinical-trial-with-lead-product-nbtxr3/, retrieved on Mar. 12, 2012, pp. 1-2.

Sargentis, C. et al "Simple method for the fabrication of a high dielectric constant metal-oxide-semiconductor capacitor embedded with Pt nanoparticles" *Applied Physics Letters*, Feb. 15, 2006, pp. 73106-1-73106-3, vol. 88, No. 7.

Written Opinion in International Application No. PCT/EP2012/075731, dated Jan. 28, 2013, pp. 1-6.

Shevchenko, E.V., et al., "Gold/Iron Oxide Core/Hollow-Shell Nanoparticles," *Advanced Materials*, 2008, vol. 20, pp. 4323-4329.

Chithrani, B. D. et al. "Determining the Size and Shape Dependence of Gold Nanoparticle Uptake into Mammalian Cells" *Nano Letters*, 2006, pp. 662-668, vol. 6. No. 4.

(56) References Cited

OTHER PUBLICATIONS

Hofmann-Amtenbrink, M. et al. "Superparamagnetic nanoparticles for biomedical applications" *Nanostructured Materials for Biomedical Applications*, 2009, 119-149.

Jong, W. et al. "Drug delivery and nanoparticles:Applications and hazards" *International Journal of Nanmedicine*, 2008, pp. 133-149, vol. 3, No. 2.

Lorenzato, C. et al. "MRI contrast variation of thermosensitive magnetoliposomes triggered by focused ultrasound: a tool for image-guided local drug delivery" *Contrast Media Mol. Imaging*, 2013, pp. 185-192, vol. 8.

Taglienti, A., et al., "Kinetics of drug release from a hyaluronan-steroid conjugate investigated by NMR spectroscopy," *Carbohydrate Research*, 2009, vol. 344, pp. 245-249.

Motosugi, U. et al. "II The Latest Trend of MRI Contrast Agent, Emergence of liver-specific contrast agent for possible bolus injection, 1. SPIO Formulation" *Innervision*, (17-9), 2002, pp. 23-25.

Salomir, R. et al. "Local Delivery of Magnetic Resonance (MR) Contrast Agent in Kidney Using Thermosensitive Liposomes and MR Imaging•Guided Local Byperthermia: A Feasibility Study In Vivo" *Journal of Magnetic Resonance Imaging*, 2005, pp. 534-540, vol. 22.

Kato, Y. et al. "Monitoring of Release of Cargo :From Nanocarriers by MRI/MR Spectroscopy (MRS): Significance of $T_2/T^*_2$ Effect of Iron Particles" *Magnetic Resonance in Medicine*, 2009, pp. 1059-1065, vol. 61.

Herrera, A., et al., "Breakthrough concept in local treatment for advanced tumors," NTBX Chicago, Jun. 3, 2013, pp. 1-51.

Pottier, A., et al., "New Use of Metals as Nanosized Radioenhancers," *Anticancer Research*, Jan. 2014, vol. 34, No. 1, pp. 443-453.

Written Opinion in International Application No. PCT/EP2014/051367, dated May 20, 2014, pp. 1-8.

Bowen, P., "Particle Size Distribution Measurement from Millimeters to Nanometers and from Rods to Platelets," *Journal of Dispersion Science and Technology*, Jan. 1, 2002, vol. 23, No. 5, pp. 631-662.

Written Opinion in International Application No. PCT/EP2014/061296, dated Sep. 5, 2014, pp. 1-9.

Yu, S. et al. "Carboxyl group ($-CO_2H$) functionalized ferrimagnetic iron oxide nanoparticles for potential bio-applications" *Journal of Materials Chemistry*, 2004, pp. 2781-2786, vol. 14.

Ismail, M.F. et al. "Potential therapeutic effect of nanobased formulation of rivastigmine on rat model of Alzheimer's disease" *International Journal of Nanomedicine*, 2013, pp. 393-406, vol. 8.

Written Opinion in International Application No. PCT/EP2014/062947, dated Jul. 21, 2014, pp. 1-4.

Ahmad, M. et al. "Synthesis of Silver Nanoparticles in Chitosan, Gelatin and Chitosan/Gelatin Bionanocomposites by a Chemical Reducing Agent and Their Characterization" *Molecules*, 2011, pp. 7237-7248, vol. 16.

U.S. Appl. No. 61/759,852, filed Feb. 1, 2013.

Guo, Z.X., et al., "Generation of alginate gel particles with AuNPs layers by polydimethylsiloxane template," *Biomicrofluidics*, Jan. 1, 2011, vol. 5, No. 2, pp. 026502-026502-6.

Ikegami, S., et al., "Effect of Viscous Indigestible Polysaccharides on Pancreatic-Biliary Secretion and Digestive Organs in Rats," *Journal of Nutrition*, Jan. 1, 1990, vol. 120, No. 4, pp. 353-360.

Witteveen, J.A., et al., "Gelatin/glycerol coating to preserve mechanically compliant nanowire electrodes from damage during brain implantation," *Journal of Vacuum Science & Technology B*, Nov./Dec. 2010, vol. 28, No. 6, pp. C6K13-C6K16.

Written Opinion in International Application No. PCT/EP2014/062976, dated Aug. 28, 2014, pp. 1-5.

DeKrafft, K.E. et al. "Zr- and Hf-based nanoscale metal-organic frameworks as contrast agents for computed tomography" *Journal of Materials Chemistry*, Sep. 21, 2012, pp. 18139-18144, vol. 22, No. 35.

Written Opinion in International Application No. PCT/EP2014/078619, dated Mar. 26, 2015, pp. 1-6.

Pernodet, N. et al. "Adverse Effects of Citrate/Gold Nanoparticles on Human Dermal Fibroblasts" *Small*, 2006, pp. 766-773, vol. 2, No. 6.

Newkirk, CE. et al. "Comparative study of hematological responses to platinum group metals, antimony and silver nanoparticles in animal models" *J Environ Sci Health A Tox Hazard Subst Environ Eng*, 2014, pp. 269-80, vol. 49, No. 3. Abstract only.

Noel, C. et al. "Gold nanoparticles induce apoptosis, endoplasmic reticulum stress events and cleavage of cytoskeletal proteins in human neutrophils" *Toxicol In Vitro*, Mar. 2016, pp. 12-22, vol. 31.

Lee, U. et al. "Cytotoxicity of gold nanoparticles in human neural precursor cells and rat cerebral cortex" *Journal of Bioscience Bioengineering*, Mar. 2016, pp. 341-344, vol. 121, No. 3.

Li, C.-H. et al. "Gold Nanoparticles Increase Endothelial Paracellular Permeability by Altering Components of Endothelial Tight Junctions, and Increase Blood-Brain Barrier Permeability in Mice" *Toxicological Sciences*, Nov. 2015, pp. 192-203, vol. 148, No. 1.

Jain, S. et al., "Cell-Specific Radiosensitization by Gold Nanoparticles At Megavoltage Radiation Energies" *Int. J. Radiation Oncology Biol. Phys.*, 2011, pp. 531-539, vol. 79, No. 2.

Understandingnano, "Nanoparticles for enhanced x-ray treatment of cancer tumors", accessed from: http://www.understandingnano.com/nanomedicine-nanoparticle-xray-cancer-treatment.html; Jul. 2009, pp. 1-2.

Nanobiotix, "Release / Nanobiotix Starts Clinical Trial with Lead Product NBTXR3," Sep. 13, 2011, XP002671267, p. 1, retrieved from internet: URL:http://www. nanobiotix.com/news/release/nanobiatix-starts-clinic-trial-with-lead-product-nbtxr3/, retrieved on Mar. 12, 2012.

Miller, T. R. et al. "Measurement of Tumor Volume By Pet to Evaluate Prognosis in Patients With Advanced Cervical Cancer Treated by Radiation Therapy" *Int. J. Radiation Oncology Biol. Phys.*, 2002, pp. 353-359, vol. 53, No. 2.

Bush, D. A. et al. "Proton-Beam Radiotherapy for Early-Stage Lung Cancer" *Chest*, Nov. 1999, pp. 1313-1319, vol. 116, No. 5.

Abu Lila, A. S. et al. "Oxaliplatin encapsulated in PEG-coated cationic liposomes induces significant tumor growth suppression via a dual-targeting approach in a murine solid tumor model" *Journal of Controlled Release*, 2009, pp. 8-14, vol. 137.

Gabizon, A. A. "Liposome circulation time and tumor targeting: implications for cancer chemotherapy" *Advanced Drug Delivery Reviews*, 1995, pp. 285-294, vol. 16.

Harashima, H. et al. "Size Dependent Liposome Degradation in Blood: In Vivo/In Vitro Correlation by Kinetic Modeling" *Journal of Drug Targeting*, 1995, pp. 253-261, vol. 3.

Hadaruga, D. I. et al. "Liposomes containing titanium dioxide nanoparticles (Short communication)" *Journal of Agroalimentary Processes and Technologies*, 2010, pp. 62-66, vol. 16, No. 1.

Shamsipour, F. et al. "Conjugation of Monoclonal Antibodies to Super Paramagnetic Iron Oxide Nanoparticles for Detection of her2/neu Antigen on Breast Cancer Cell Lines" *Journal of Medical Biotechnology*, Apr.-Jun. 2009, pp. 27-31, vol. 1, No. 1.

Kim, J-Y. et al. "In-vivo tumor targeting of pluronic-based nanocarriers" *Journal of Controlled Release*, 2010, pp. 109-117, vol. 147.

Yu, M. K. et al. "Drug-Loaded Superparamagnetic Iron Oxide Nanoparticles for Combined Cancer Imaging and Therapy In Vivo" *Angew. Chem. Int. Ed.*, 2008, pp. 5362-5365, vol. 47.

Choi, W. I. et al. "The effect of mechanical properties of iron oxide nanoparticle-loaded functional nano-carrier on tumor targeting and imaging" *Journal of Controlled Release*, 2012, pp. 267-275, vol. 162.

Liang, X. et al. "Mechanical properties and stability measurement of cholesterol-containing liposome on mica by atomic force microscopy" Journal of Colloid and Interface Science, 2004, pp. 53-62, vol. 278.

Nie, Y. et al. "Cholesterol Derivatives Based Charged Liposomes for Doxorubicin Delivery: Preparation, In Vitro and In Vivo Characterization" *Theranostics*, 2012, pp. 1092-1103, vol. 2, No. 11.

Bhatt, N. et al. "Stability study of O/W emulsions using zeta potential" *Journal of Chemical and Pharmaceutical Research*, 2010, pp. 512-527, vol. 2, No. 1.

(56) References Cited

OTHER PUBLICATIONS

Thongborisute, J. et al. "Properties of Liposomes coated with hydrophobically modified chitosan in oral liposomal drug delivery" *Pharmazie*, 2006, pp. 106-111, vol. 61.

Ogu, C. C. et al. "Drug interactions due to cytochrome P450" *BUMC Proceedings*, Oct. 2000, pp. 421-423, vol. 13.

Babcock, J. J. et al. "Bovine serum albumin oligomers in the E- and B-forms at low protein concentration and ionic strength" *International Journal of Biological Macromolecules*, Feb. 1, 2013, pp. 42-53, vol. 53.

Ma, P. et al. "Paclitaxel Nano-Delivery Systems: A Comprehensive Review" *Journal of Nanomedicine and Nanotechnology*, Jan. 1, 2013, pp. 1-16, vol. 4, No. 2.

Written Opinion in International Application No. PCT/EP2015/077423, dated Jan. 21, 2016, pp. 1-5.

He, C. et al. "Effects of particle size and surface charge on cellular uptake and biodistribution of polymeric nanoparticles" *Biomaterials*, May 1 2010, pp. 3657-3666, vol. 31, No. 13.

"NCL Method PCC-2 Measuring Zeta Potential of Nanoparticles" Nov. 1, 2009, Retrieved from the IntRL:http://ncl.cancer.gov/NCL_Method_PCC-2.pdf on Feb. 23, 2015, pp. 1-14.

Written Opinion in International Application No. PCT/EP2015/077446, dated Feb. 3, 2016, pp. 1-6.

Banquy, X. et al. "Effect of mechanical properties of hydrogel nanoparticles on macrophage cell uptake" *Soft Matter*, Jan. 1, 2009, pp. 3984-3991, vol. 5, No. 20.

Written Opinion in International Application No. PCT/EP2015/077438, dated Jan. 27, 2016, pp. 1-7.

Written Opinion in International Application No. PCT/EP2015/077425, dated Jan. 15, 2016, pp. 1-6.

Belisario, M. A. et al. "Effect of avarol, avarone and nine of their natural and synthetic derivatives on microsomal drug-metabolizing enzymes" *Toxicology Letters*, 1991, pp. 183-193, vol. 57.

Michalets, E. L. et al. "Update: Clinically Significant Cytochrome P-450 Drug Interactions" *Pharmacotherapy*, 1998, pp. 84-112, vol. 18, No. 1.

Written Opinion in International Application No. PCT/EP2015/077441, dated Feb. 3, 2016, pp. 1-6.

Abra, RM. et al. "Liposome Disposition in Vivo: Effects of Pre-Dosing with Liposomes" *Research Communications in Chemical Pathology and Pharmacology*, Aug. 1980, pp. 349-360, vol. 29, No. 2.

Olson, F. et al. "Preparation of Liposomes of Defined Size Distribution by Extrusion Through Polycarbonate Membranes" *Biochimica et Biophysica Acta*, 1979, pp. 9-23, vol. 557.

Lu, H. et al. "Drug-target residence time: critical information for lead optimization" *Current Opinion in Chemical Biology*, 2010, pp. 467-474, vol. 14.

Copeland, R. A. et al. "Drug-target residence time and its implications for lead optimization" *Nature Reviews/Drug Discovery*, Sep. 2006, pp. 730-739, Corrigendum (1 page), vol. 5.

Simoes, S. et al. "Cationic liposomes for gene delivery" *Expert Opinion in Drug Delivery*, 2005, pp. 237-254, vol. 2, No. 2.

Singh, R. et al. "Nanoparticle-based targeted drug delivery" *Experimental and Molecular Pathology*, 2009, pp. 215-223, vol. 86.

Lai, B.-H. et al. "Surface modification of iron oxide nanoparticles with polyarginine as a highly positively charged magnetic nano-adsorbent for fast and effective recovery of acid proteins" *Process Biochemistry*, 2012, pp. 799-805, vol. 47.

Zhao, S. et al. "Preparation and Properties of Supramolecular Hydrogels Hybridized with Au Nanoparticles" *ACTA CHIMICA SINICA*, 2011, pp. 492-496, vol. 69, No. 4.

Viscosity (https://www.saylor.org/site/wp-content/uploads/2011/04Niscosity.pdf (downloaded Jul. 23, 2018), pp. 1-20.

Noizat-Pirenne, F. et al. "Rituximab for prevention of delayed hemolytic transfusion reaction in sickle cell disease" *Haematologica*, 2007, pp. 132-135, vol. 92.

Milojevic, J. et al., "Stoichiometry and Affinity of the Human Serum Albumin-Alzheimer's Aβ Peptide Interactions" *Biophysical Journal*, 2011, pp. 183-192, vol. 100.

Liumbruno, G. et al., "Recommendations for the use of albumin and immunoglobulins" *Blood Transfus*, 2009, pp. 216-234, vol. 7.

Thompson, K. M. et al., "Human monoclonal antibodies specific for blood group antigens demonstrate multispecific properties characteristic of natural autoantibodies" *Immunology*, 1992, pp. 146-157, vol. 76.

Crittenden, M. et al. "Current Clinical Trials Testing Combinations of Immunotherapy and Radiation" *Semin Radiat Oncol*, Jan. 2015, pp. 54-64, vol. 25, No. 1, abstract 1 page.

Graf, M.R. et al. "Irradiated tumor cell vaccine for treatment of an established glioma. I. Successful treatment with combined radiotherapy and cellular vaccination" *Cancer Immunol Immunother*, 2002, pp. 179-189, vol. 51.

Guo, C. et al. "Therapeutic Cancer Vaccines: Past, Present and Future" *Adv Cancer Res.*, 2013, pp. 1-45, vol. 119.

Golden, E. B. et al. "Radiotherapy and Immunogenic Cell Death" *Seminars in Radiation Oncology*, 2015, pp. 11-17, vol. 25.

Vatner, R. E et al. "Combinations of immunotherapy and radiation in cancer therapy" *Frontiers in Oncology*, Nov. 28, 2014, pp. 1-15, vol. 4, Article 325.

\* cited by examiner

NANOPARTICLES FOR USE AS A THERAPEUTIC VACCINE

CROSS-REFERENCE TO RELATED APPLICATION

This application is the U.S. national stage application of International Patent Application No. PCT/EP2016/061989, filed May 27, 2016.

FIELD OF THE INVENTION

The present invention relates to the field of human health and more particularly concerns nanoparticles for use as a therapeutic vaccine, as such or included in a composition, in the context of radiotherapy in a subject suffering of a cancer, in particular of a metastatic cancer or of a liquid cancer. The nanoparticles whose use is herein described consist in a material having a density of at least 7 g/cm$^3$ and an atomic number (Z) of at least 25. Each nanoparticle is covered with a biocompatible coating allowing its stability between pH 6.5 and 7.5 in a physiological fluid. When irradiated, these nanoparticles are capable of boosting the destruction of cancer cells thanks to an optimized stimulation of the subject's own immune system when compared to the cancer cells' destruction obtained with radiotherapy alone, in particular in a subject suffering from a metastatic cancer, preferably in a subject suffering from metastatic cancer and undergoing a palliative radiotherapy, in a subject suffering from metastatic cancer for whom (curative) radiotherapy has been abandoned, in a subject suffering from a cancer which is not (conventionally) treated by radiotherapy, and in a subject suffering from a liquid cancer. Thanks to the present invention, irradiation doses administered to the subject in the context of radiotherapy, preferably in the context of a fractionated radiotherapy, are significantly more efficient in terms of cancer cell destruction without adversely affecting surrounding healthy tissue more. The present description in addition discloses new compositions and kits as well as uses thereof.

BACKGROUND

Cancer is a leading cause of death worldwide, which accounted for 8.2 million deaths in 2012. It is expected that annual cancer cases will rise from 14 million in 2012 to 22 within the next two decades (WHO). Cancer may grow locally and/or spread systemically through lymphatic or hematogenous routes.

Surgery, radiation therapy, and pharmaceuticals, in particular chemotherapeutic drugs, are of central importance in the treatment of cancer, each of which can be used alone or in combination, to address all sites at risk for harboring disease, depending on the type of cancer being treated. For a malignancy to be cured, it must be controlled at both the local and systemic levels.

In spite of recent advances in the detection and treatment of some malignancies, metastases remain common and account for approximately 80-90% of cancer deaths. The standard treatment for metastatic disease in most patient cancers is systemic cytotoxic chemotherapy and hormonal deprivation (Dhara M. MacDermed et al. Journal of Surgical Oncology 2008). There is a vital need for the development of novel curative therapies for the treatment of patients with metastatic cancer.

Some specific tumors/cancers have an affinity to spread to selected organs. The most common sites of metastases are lungs (e.g. when the primary cancer is a sarcoma), liver (e.g. .g. when the primary cancer is a gastrointestinal cancer), bones (e.g. .g. when the primary cancer is a breast or a prostate cancer) and the brain (e.g. .g. when the primary cancer is a lung cancer, a renal cancer, or a melanoma).

Radiotherapy is the second most used treatment of cancer, ahead of pharmaceuticals, with an estimated half of all newly diagnosed cancer patients receiving radiotherapy at some point in the course of their disease. Radiation therapy uses high-energy particles or waves, such as X-rays, gamma rays, electron beams, or protons, to destroy or damage cancer cells.

The therapeutic use of local ionizing radiation has been largely guided by a strategy designed to achieve the goal of effectively eliminating cancer cells. Radiotherapy as a sole therapeutic modality can offer the possibility for organ functional preservation, such as in the context of bladder and laryngeal cancers. As an adjuvant therapy, radiotherapy can facilitate resection when given before surgery, or treat microscopic residual disease when given after surgery, such as treatment after breast-conserving lumpectomy. A new development is the use of stereotactic body radiotherapy (SBRT) to ablate sites of oligometastatic disease. SBRT enables highly focal treatment of cancer with single or few fractions of high-dose radiations (typically between 5 Gy and 25 Gy). The existence of an oligometastatic state is based on an "intermediate between purely localized lesions and those widely metastatic". Typically between 1 up to 5, for example 1, 2, 3, 4 or 5, metastases or metastatic lesions are considered for SBRT (Dhara M. MacDermed et al. Journal of Surgical Oncology 2008; Ralph R. Weichselbaum Nat. Rev. Clin. Oncol. 2011).

However, metastatic malignancies with many distant metastases (typically more than 5, preferably more than 6, 7, 8, 9, 10, 11, 12, 13, 14, 15, 16, 17, 18, 19 or 20 metastases) are associated with a poor prognosis (Ralph R. Weichselbaum Nat. Rev. Clin. Oncol. 2011).

Patients with widespread systemic diseases (patients exhibiting many metastases also identified as "polymetastatic" patients) are typically not considered by the oncologist as curable by current regional treatment such as radiotherapy. On the other hand, palliative radiotherapy is used for palliation of symptoms and is distinct from radiotherapy delivered as curative treatment (Sonam Sharma et al. Seminars in Oncology 2014). Palliative radiotherapy is an efficacious treatment for many symptoms from locally advanced or metastatic tumors, even for patients with short life expectancy (Sonam Sharma et al. Seminars in Oncology 2014). Here, radiotherapy can be an effective treatment for pain, neurologic symptoms, relief of obstructive symptoms (such as biliary or urinary tract obstructions) and relief from bleeding or ulcerated lesions. Palliative radiotherapy may also be used to assist with maintenance of local tumor control in area likely to be affected and become symptomatic. Typical dose-fractionation schemes in palliative radiotherapy are the followings:

1×8 Gy, 5-6×4 Gy, 10×3 Gy for uncomplicated bone metastases and for 1 day up to 2 weeks;

5×4 Gy; 10×3 Gy, 15×2.5 Gy for whole brain radiotherapy and for 1 up to 3 weeks;

2×7.5-8.5 Gy, 10×3 Gy, 15×2.5 Gy for advanced cancer in lung causing airway obstruction, superior vena cava syndrome and for 1 up to 3 weeks;

1×8-10 Gy, 5×4 Gy, 10×3 Gy, 15-30×2-3 Gy for visceral metastases causing pain, symptoms of obstruction, bleeding and for 1 day up to 6 weeks;

1-5×6-24 Gy for stereotactic radiotherapy generally reserved for patients with good performance status, with expected long prognosis and/or with few metastases and for 1 up to 5 days (Sonam Sharma et al. Seminars in Oncology 2014, Table 3).

Besides, available evidence suggests that local radiation at clinically therapeutic doses elicits some activation of the innate and adaptive immune system. Radiation has been shown to induce an immunogenic cell death (ICD), potentially converting a tumor into in situ vaccine, characterized in particular by three molecular signals that promote uptake of dying cells by dendritic cells, cross-presentation of the tumor-derived antigens to T cells, and activation of anti-tumor T cells including activation of cytotoxic CD8+ T cells: exposure of calreticulin (CRT) on the tumor cell surface, release of high-mobility group protein B1 (HMGB1), and release of Padenosine triphosphate (ATP) (Oliver Kepp et al. Oncoimmunology 2014).

It is also known that tumor response to radiations includes DNA damages and that sensing of tumor-derived DNA may trigger IFN production and generate anti-tumor T-cell responses to immunogenic tumors (see for instance Theresa L. Whiteside et al. 2016).

Radiation is a complex modifier of tumor microenvironment and, by itself, is seldom sufficient to induce a therapeutically significant anti-tumor immune response, since it can also detrimentally activate immune suppressive pathway. The proportion of tumor cells undergoing ICD and the remodeling of tumor microenvironment after radiation are variable. The results of this balance ultimately determine the ability of radiation to convert dying cancer cells into an effective in situ vaccine (Sandra Demaria and Silvia C. Formenti, 2012).

Combinations of radiation with immunotherapeutic agents have been reported to stimulate the immune response. Cytokines [interleukin-2 (IL2) and interferon-alpha (IFNα)] have been used for decades as therapeutic approach. Today, numerous strategies for overcoming tumor immune evasion are under evaluation. Example of immunotherapeutic approaches under clinical evaluation include (1) T-cell checkpoint inhibitors or agonists for T-cell activation pathway (2) novel cytokines such as IL12 and IL15, (3) therapeutic vaccine, (4) elimination of immunosuppressive cells and (5) other agents and approaches designed to enhance immune cell function (Scott J. Antonia et al. 2014; Theresa L. Whiteside et al. 2016).

However, producing effective treatment vaccines remains difficult and challenging. To be effective, cancer treatment vaccines must achieve two goals. First, they must stimulate specific immune responses against the correct target cells (i.e. cancer cells). Second, the immune responses must be powerful enough to overcome the barriers that these cells use to protect themselves from attack by the host immune systems, typically by B cells and natural killer T cells.

SUMMARY OF THE INVENTION

Inventors now herein describe the advantageous use of a nanoparticle and/or aggregate of nanoparticles as a therapeutic vaccine, as such or included in a composition (which is typically a therapeutic composition, in particular a vaccine composition), in a subject suffering of a cancer and exposed to radiotherapy. The nanoparticle and/or aggregate of nanoparticles as well as the composition comprising a nanoparticle and/or aggregate of nanoparticles is typically for use for treating cancer. The combination of such nanoparticles with radiotherapy significantly enhances the host's anti-cancer immune response and optimizes the global treatment, in particular in the context of a fractioned radiotherapy comprising at least one irradiation step wherein the ionizing radiation dose ranges from 1.8 to 30 Gray (Gy), preferably 1.8 to 20 Gray (Gy), typically from 2 to 15 Gray (Gy). The present invention is particularly efficient towards metastatic cancer when the cancer has evolved into a widespread systemic disease (as defined herein above) thanks to the abscopal effect allowed by the technology, and towards liquid cancer, and favors a complete and permanent anti-tumor activity.

The abscopal effect is a phenomenon observed in the treatment of metastatic cancer where localized irradiation of a particular tumor site causes a response in a site distant to the irradiated volume. Radiotherapy may help reverse the tolerance to weakly immunogenic tumour-associated antigens in order to elicit an anticancer immune response. However, the abscopal effect has remained a rare clinical event when radiotherapy is used alone. Kobe Reynders et al. reported 23 clinical cases of abscopal affect after radiotherapy between 1973 and 2013 (Kobe Reynders et al. Cancer Treatment Review 2015).

Thanks to the present invention local irradiation is able to elicit the development of a sustained anti-tumor response when compared to radiotherapy alone thereby enhancing the control of the tumor both locally and systemically.

Examples herein provided for the first time by inventors demonstrate the in vitro amplification of damage associated molecular patterns (DAMPs) induced by dying cancer cells [the herein tested cancer cell lines including radiosensitive cell lines (such as the human colorectal HCT 116 cancer cell line) and radioresistant cell lines (such as the human glioblastoma 42 MG BA cell line or the human pancreas PANC-1 cancer cell line)] when using the nanoparticle and/or aggregate of nanoparticles as a therapeutic vaccine.

Of upmost interest, vaccination of immunocompetent mice with murine colorectal CT-26 cancer cell treated with the nanoparticles and/or aggregates of nanoparticles of the present invention and irradiated in vitro, markedly prevent the formation of a tumor when the animal are challenged 7 days later with healthy/living CT-26 cancer cells, when compared to radiotherapy alone. Such results surprisingly demonstrate that the combination of nanoparticles of the invention with radiotherapy amplify the immune response and transform dying cancer cells into an efficient vaccine directed against cancer cells.

In a preferred aspect, the herein described products of the invention (nanoparticle and/or aggregate of nanoparticles and compositions comprising such a nanoparticle and/or aggregate of nanoparticles) are preferably for use in a subject selected from a subject suffering from metastatic cancer and undergoing a palliative radiotherapy, a subject suffering from metastatic cancer for whom (curative) radiotherapy has been abandoned, a subject suffering from a cancer which is not (conventionally) treated by radiotherapy, and a subject suffering from a liquid cancer, and are preferably for use in a subject selected from a subject suffering from metastatic cancer and undergoing a palliative radiotherapy, a subject suffering from metastatic cancer for whom (curative) radiotherapy has been abandoned, and a subject suffering from a liquid cancer.

The subject suffering from a metastatic cancer is typically a subject as herein defined suffering of a cancer having many distant metastases which has typically evolved into a widespread systemic disease. Subjects having many distant metastases are also herein identified as a "polymetastatic" subject or patient.

Herein described is thus a nanoparticle and/or aggregate of nanoparticles for use as a therapeutic vaccine, or a nanoparticle and/or aggregate of nanoparticles for use for preparing a therapeutic composition, typically a vaccine composition, for use (typically for use for treating cancer) in a subject suffering from a cancer, typically from a metastatic cancer [metastatic cancer being herein typically defined as involving many/numerous distant metastases and being typically considered as associated to a widespread systemic disease], from a cancer which is not (conventionally) treated by radiotherapy, or from a liquid cancer, in the context of fractionated radiotherapy comprising at least one irradiation step wherein the ionizing radiation dose ranges from 1.8 to 30 Gray (Gy), preferably 1.8 to 20 Gray (Gy), typically from 2 to 15 Gray (Gy), and wherein each nanoparticle consists in a material having a density of at least 7 g/cm$^3$ and an atomic number (Z) of at least 25, and each nanoparticle or aggregate of nanoparticles is covered with a biocompatible coating allowing the nanoparticle stability between pH 6.5 and 7.5 in a physiological fluid.

The nanoparticle and/or aggregate of nanoparticles is typically for use for treating cancer, preferably in a selected population of subjects/patients, typically in a subject suffering from metastatic cancer and undergoing a palliative radiotherapy, in a subject suffering from metastatic cancer for whom (curative) radiotherapy has been abandoned, in a subject suffering from a cancer which is not (conventionally) treated by radiotherapy, or in a subject suffering from a liquid cancer.

Also herein disclosed is a vaccine composition for use, typically for use for treating cancer, in a subject suffering from cancer, typically from a metastatic cancer (in particular a metastatic cancer where cancer has evolved into a widespread systemic disease), or from a liquid cancer, in the context of radiotherapy, preferably in the context of a fractionated radiotherapy.

A typical composition is a vaccine composition comprising a nanoparticle and/or aggregate of nanoparticles for use for treating cancer in a subject suffering from metastatic cancer and undergoing a palliative radiotherapy, in a subject suffering from metastatic cancer for whom (curative) radiotherapy has been abandoned, in a subject suffering from a cancer which is not (conventionally) treated by radiotherapy, or in a subject suffering from a liquid cancer, wherein the treatment comprises exposing the subject to a fractionated radiotherapy comprising at least one irradiation step wherein the ionizing radiations dose ranges from 1.8 to 30 Gray (Gy), preferably 1.8 to 20 Gray (Gy), and wherein each nanoparticle consists in a material having a density of at least 7 g/cm$^3$ and an atomic number (Z) of at least 25 and each nanoparticle or aggregate of nanoparticles is covered with a biocompatible coating allowing the nanoparticle stability between pH 6.5 and 7.5 in a physiological fluid.

The vaccine composition comprises a nanoparticle or aggregate of nanoparticles as herein described preferably together with a pharmaceutically acceptable carrier or vehicle. A particular vaccine composition further comprises at least one immunotherapeutic agent and optionally a therapeutic agent for treating cancer.

Also herein described is the use of a nanoparticle or aggregate of nanoparticles or a therapeutic composition as herein defined for treating cancer in a subject, preferably in selected populations of subjects/patients, typically in a subject suffering from metastatic cancer and undergoing a palliative radiotherapy, in a subject suffering from metastatic cancer for whom (curative) radiotherapy has been abandoned, in a subject suffering from a cancer which is not (conventionally) treated by radiotherapy, or in a subject suffering from a liquid cancer, as well as the corresponding methods for treating cancer in a subject in need thereof comprising a step of administering to said subject a nanoparticle or aggregate of nanoparticles or a therapeutic composition as herein defined.

Further herein provided is a kit, typically a vaccine kit, comprising (i) a nanoparticle or aggregate of nanoparticles as herein described, or a composition comprising such a nanoparticle or aggregate of nanoparticles, preferably together with (ii) at least one immunotherapeutic agent and/or therapeutic agent for treating cancer.

It is well known to adapt in vitro the dose (delivered in a single fraction) to the radiosensitivity of the cancer cells. Radiosensitive cancer cell line such as the HCT 116 cell line may receive lower radiation dose when compared to more radio resistant cancer cell lines such as the 42 MG BA and the PANC-1 cell lines. The increased generation of DAMPs observed in vitro anticipates an enhance immune response in vivo.

Figure 4:
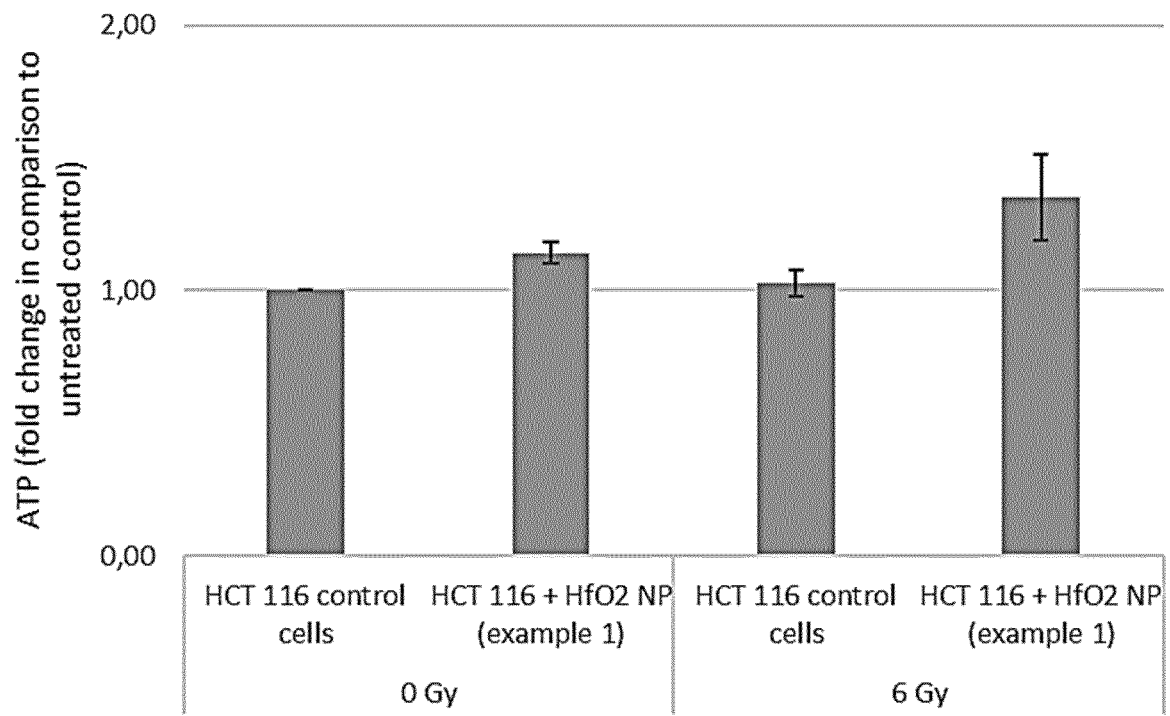

FIG. 4: ATP secretion from HCT 116 cancer cells treated or not with HfO$_2$ nanoparticles (NPs) suspension from example 1 and exposed or not to radiotherapy (6 Gy delivered in a single fraction) is reported as fold-change in comparison to untreated control.

Figure 5:
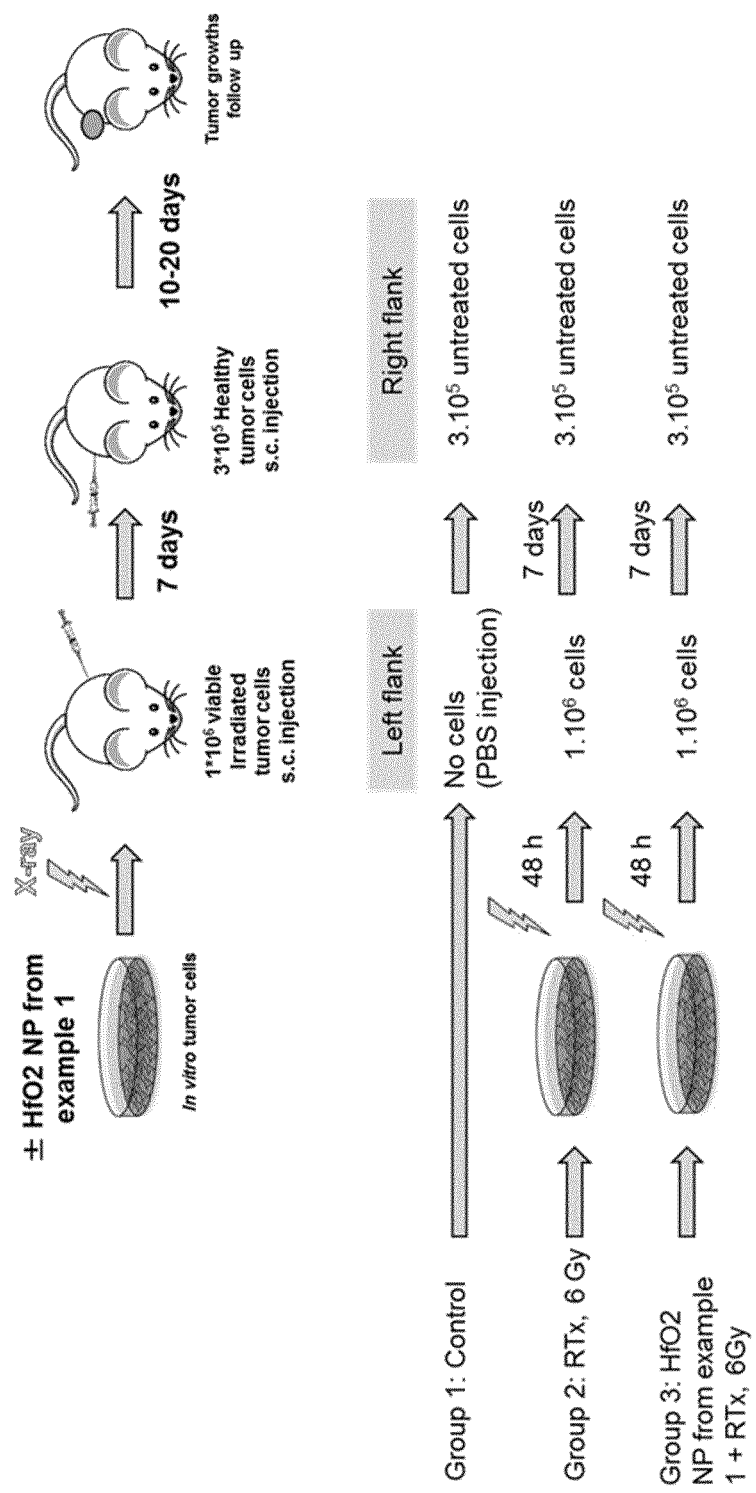

FIG. 5: Illustration of the vaccination assay protocol performed with the murine colorectal CT-26 cell line in immunocompetent mice, presenting the schedule of injection for the three groups, group 1 (control group), group 2 (irradiation group: 6 Gy delivered in a single fraction) and group 3 (HfO$_2$ NPs from example 1 exposed to irradiation: 6 Gy delivered in a single fraction).

Figure 6:
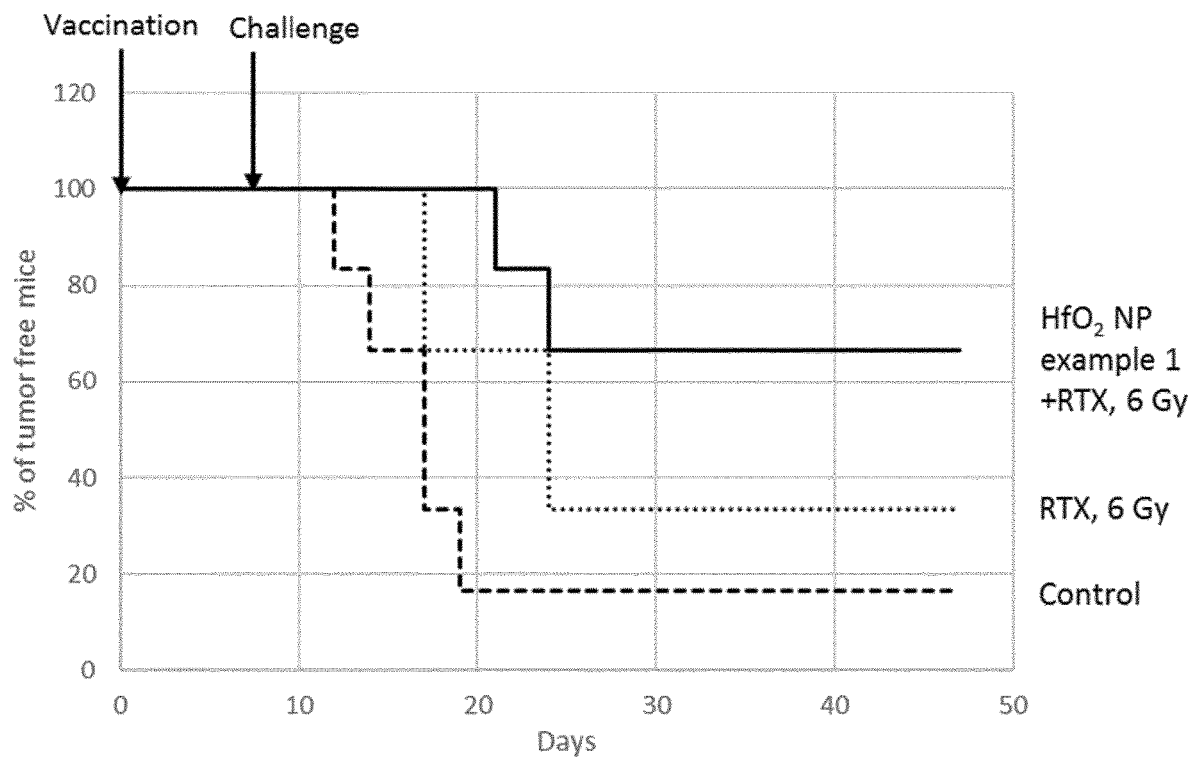

FIG. 6: vaccination assay protocol where the percentage of tumor free mice for group 1 (control), group 2 (RTx, 6 Gy) and group 3 (HfO$_2$ NP example 1+RTx, 6 Gy) is presented as function of the days post vaccination.

DETAILED DESCRIPTION OF THE INVENTION

Radiotherapy

Nanoparticle and/or aggregate of nanoparticles as well as any composition comprising such nanoparticle and/or aggregate of nanoparticles are herein described for use as a therapeutic composition or vaccine (composition) in a subject suffering from a cancer, in particular from a metastatic cancer, preferably from a metastatic cancer where cancer has evolved into a widespread systemic disease, or from a liquid cancer, in the context of radiotherapy, i.e. in a subject to whom nanoparticles have been administered and who is then exposed to radiotherapy. In other words to become usable as a therapeutic vaccine, nanoparticles are to be exposed to ionizing radiations which means that they are used in combination with radiotherapy.

A cancer which has evolved into a widespread systemic disease typically involves many distant metastases, typically more than 5, preferably more than 6, 7, 8, 9, 10, 11, 12, 13, 14, 15, 16, 17, 18, 19 or 20 metastases, and is most of the time associated with a poor prognosis (cf. Ralph R. Weichselbaum Nat. Rev. Clin. Oncol. 2011). The subject suffering from such a cancer may further comprise in addition to the metastatic lesions/sites associated to said cancer other cancer cells sites/lesions which are primary and/or metastatic cancer lesions associated to a distinct primary cancer/tumor.

A particular composition herein described is a vaccine composition comprising a nanoparticle and/or aggregate of nanoparticles for use for treating cancer in a subject suffering from metastatic cancer and undergoing a palliative radiotherapy, in a subject suffering from metastatic cancer for whom radiotherapy has been abandoned (typically has been abandoned as a (global) curative treatment), in a subject suffering from a cancer which is not (conventionally/classically) treated by radiotherapy, or in a subject suffering from a liquid cancer, wherein the treatment comprises exposing the subject to a fractionated radiotherapy comprising at least one irradiation step wherein the ionizing radiations dose ranges from 1.8 to 30 Gray (Gy), preferably 1.8 to 20 Gray (Gy), and wherein each nanoparticle consists in a material having a density of at least 7 g/cm$^3$ and an atomic number (Z) of at least 25 and each nanoparticle or aggregate of nanoparticles is covered with a biocompatible coating allowing the nanoparticle stability between pH 6.5 and 7.5 in a physiological fluid.

In the context of the present invention, the subject or patient is a mammal. In a particular embodiment, the mammal is a human being, whatever its age or sex. The subject suffers from a cancer.

A preferred subject likely to benefit from the invention typically suffers from a solid cancer or from a liquid cancer.

In a particular aspect, the subject suffers from a cancer classically treated by radiotherapy or where radiotherapy is a classical treatment or is the most appropriate treatment for a particular subject, or where radiotherapy could be indicated.

In another particular and preferred aspect, the subject who will beneficiate from the present invention is a subject who suffers from a cancer where radiotherapy would not be considered as a treatment option (or in other words is not considered as a conventional treatment or possible curative treatment for the considered subject, or is only used against one or a few, typically less than five cancer cells sites/lesions, said lesions being metastatic or primary cancer lesions among numerous cancer cells sites/lesions present in the subject) or would no longer be considered as a (curative) treatment option, typically when the subject is under palliative treatment or when radiotherapy was abandoned. When under palliative treatment, the subject is still exposed to radiotherapy but said radiotherapy can no longer be considered as a curative radiotherapy.

In this context, the subject is preferably a subject suffering from a metastatic cancer with many/numerous and distant metastases (i.e. widespread metastases), typically more than 5, preferably more than 6, 7, 8, 9, 10, 11, 12, 13, 14, 15, 16, 17, 18, 19 or 20 metastases, as explained previously.

In other words, the nanoparticles and/or aggregates of nanoparticles of the present invention, when exposed to ionizing radiations, could offer a solution to patients' populations for which radiotherapy is not considered by the oncologist as a curative treatment.

The present invention now offers to such particular subjects a curative cancer treatment option.

A typical subject suffering from a cancer likely to benefit from the invention is selected from a subject suffering from metastatic cancer and undergoing a palliative radiotherapy, a subject suffering from metastatic cancer for whom (curative) radiotherapy has been abandoned, a subject suffering from a cancer which is not (conventionally/classically) treated by radiotherapy, and a subject suffering from a liquid cancer. Preferably the subject is selected from a subject suffering from metastatic cancer and undergoing a palliative radiotherapy, a subject suffering from metastatic cancer for whom (curative) radiotherapy has been abandoned, and a subject suffering from a liquid cancer.

In the art and in the context of the present invention, the term "curative treatment" or "curative therapy" refers to a treatment or therapy, in particular "radiotherapy", offering to the subject to be treated a curative solution for treating the cancer(s) he/she is affected by, that is for globally treating said subject [primary tumor(s) as well as corresponding metastatic lesion(s)].

As well known by the skilled person, palliative radiotherapy is used for palliation of symptoms and is distinct from radiotherapy, i.e. radiotherapy delivered as curative treatment (also herein identified as "curative radiotherapy"). Indeed, palliative radiotherapy is considered by the skilled person as an efficacious treatment for treating many symptoms induced by locally advanced or metastatic tumors, even for patients with short life expectancy.

Typically, the metastatic cancer affects (i) a connective tissue and is preferably selected from a fibrosarcoma, myxosarcoma, liposarcoma, chondrosarcoma, osteosarcoma, chordoma, malignant fibrous histiocytoma, (ii) an endothelium or mesothelium tissue and is preferably selected from hemangiosarcoma, angiosarcoma, lymphangiosarcoma and mesothelioma, (iii) a muscle tissue and is preferably selected from leiomyosarcoma and rhabdomyosarcoma, (iv) an epithelial tissue and is preferably selected from adenocarcinoma, squamous cell carcinoma and epidermoid carcinoma, (v) a neural tissue and is preferably selected from multiform glioblastoma, glioma, neuroblastoma, medulloblastoma, meningioma, neurofibrosarcoma and schwannoma, and (vi) the APUD system and is preferably selected from thyroid carcinoma, pancreas carcinoma, stomach carcinoma and intestine carcinoma. In another preferred embodiment, the metastatic cancer is a melanoma.

The metastatic cancer can be, or can derive from, a cancer selected for example from skin cancer, central nervous system cancer, head and neck cancer, lung cancer, kidney cancer, breast cancer, gastrointestinal cancer (GIST), prostate cancer, liver cancer, colon cancer, rectum cancer, anal cancer, oesophagus cancer, male genitourinary cancer, gynecologic cancer, adrenal and retroperitoneal cancer, sarcomas of bone and soft tissue, pediatric cancer, neuroblastoma, central nervous system cancer and Ewing's sarcoma.

Typically, the liquid cancer affects blood or lymphoid cell tissue. It is typically selected from leukemia, myeloma and lymphoma.

The subject may have a tumor. Unless otherwise specified in the present disclosure, the tumor is a malignant tumor.

In another embodiment, the subject suffers from a liquid cancer where radiotherapy is indicated by the oncologist (for example lymphoma).

Preferably the radiotherapy the subject is to be exposed to is a fractionated radiotherapy, advantageously a fractionated radiotherapy comprising at least one irradiation step (also herein identified as a "fraction treatment"), typically several irradiation steps, wherein the ionizing radiations dose ranges from 1.8 to 30 Gray (Gy), preferably 1.8 to 20 Gray (Gy), preferably from 1.8 to 15 Gray (Gy), per irradiation step.

In the context of a fractioned radiotherapy the total dose of ionizing radiations is divided into several, smaller doses over a period of several days. This maximizes the effect of radiations on cancer and minimizes the negative side effects on healthy cells. Typical fractionation schemes divide the total dose into 30 units/fractions delivered every weekday over 6 weeks, though current research is considering the benefits of accelerated fractionation (2 deliveries per day and/or deliveries on weekends as well).

The term "Ionizing radiations" refers to highly-energetic particles or waves that can ionize an atom or molecule. Ionizing ability depends on the energy of individual particles or waves, and not on their number. A large flood of particles or waves will not, in the most-common situations, cause ionization if the individual particles or waves are insufficiently energetic. A typical ionizing radiation is a radiation, the energy of which is of at least 1.8 KeV.

In a preferred embodiment, the ionizing radiations dose per irradiation step is selected from 1.8, 2, 2.2, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, 6.5, 7, 7.5, 8, 8.5, 9, 9.5, 10, 11, 12, 13, 14, 15, 20, 25 and 30 Gy per fraction treatment. The ionizing radiations dose is preferably selected from 1.8, 2, 2.4, 2.5, 3, 3.2, 3.6, 4, 4.5, 5, 5.5, 6, 7, 8, 10, 15, 20, 25 and 30 Gy per fraction treatment, even more preferably from 2, 3, 5, 6, 7, 8, 10, 15, 20, 25 and 30 Gy.

Preferred fractionated radiotherapy can be selected from 25 fractions of 2 Gy (total: 50 Gy), 30 fractions of 2 Gy (total: 60 Gy), 35 fractions of 2 Gy (total: 70 Gy), 40 fractions of 2 Gy (total: 80 Gy), 5 fractions of 3 Gy (total: 15 Gy), 10 fractions of 3 Gy (total: 30 Gy), 15 fractions of 3 Gy (total: 45 Gy), 20 fractions of 3 Gy (total: 60 Gy), 25 fractions of 3 Gy (total: 75 Gy), 3 fractions of 4 Gy (total: 12 Gy), 5 fractions of 4 Gy (total: 20 Gy), 8 fractions of 4 Gy (total: 32 Gy), 10 fractions of 4 Gy (total: 40 Gy), 15 fractions of 4 Gy (total: 60 Gy), 20 fractions of 4 Gy (total: 80 Gy), 2 fractions of 5 Gy (total: 10 Gy), 3 fractions of 5 Gy (total: 15 Gy), 4 fractions of 5 Gy (total: 20 Gy), 5 fractions of 5 Gy (total: 25 Gy), 6 fractions of 5 Gy (total: 30 Gy), 8 fractions of 5 Gy (total: 40 Gy), 10 fractions of 5 Gy (total: 50 Gy), 1 fraction of 6 Gy (total: 6 Gy), 2 fractions of 6 Gy (total: 12 Gy), 3 fractions of 6 Gy (total: 18 Gy), 4 fractions of 6 Gy (total: 24 Gy), 5 fractions of 6 Gy (total: 30 Gy), 6 fractions of 6 Gy (total: 36 Gy), 10 fractions of 6 Gy (total: 60 Gy), 1 fraction of 7 Gy (total: 7 Gy), 2 fractions of 7 Gy (total: 14 Gy), 3 fractions of 7 Gy (total: 21 Gy), 4 fractions of 7 Gy (total: 28 Gy), 5 fractions of 7 Gy (total: 35 Gy), 1 fraction of 8 Gy (total: 8 Gy), 2 fractions of 8 Gy (total: 16 Gy), 3 fractions of 8 Gy (total: 24 Gy), 4 fractions of 8 Gy (total: 32 Gy), 5 fractions of 8 Gy (total: 40 Gy), 1 fraction of 9 Gy (total: 9 Gy), 2 fractions of 9 Gy (total: 18 Gy), 3 fractions of 9 Gy (total: 27 Gy), 4 fractions of 9 Gy (total: 36 Gy), 5 fractions of 9 Gy (total: 45 Gy), 1 fraction of 10 Gy (total: 10 Gy), 2 fractions of 10 Gy (total: 20 Gy), 3 fractions of 10 Gy (total: 30 Gy), 4 fractions of 10 Gy (total: 40 Gy), 1 fraction of 15 Gy (total: 15 Gy), 2 fractions of 15 Gy (total: 30 Gy), 3 fractions of 15 Gy (total: 45 Gy), 4 fractions of 15 Gy (total: 60 Gy), 1 fraction of 20 Gy (total: 20 Gy), 2 fractions of 20 Gy (total: 40 Gy), 3 fractions of 20 Gy (total: 60 Gy), 1 fraction of 25 Gy (total: 25 Gy), 2 fractions of 25 Gy (total: 50 Gy), 3 fractions of 25 Gy (total: 75 Gy), 1 fraction of 30 Gy (total: 30 Gy), and 2 fractions of 30 Gy (total: 60 Gy).

In a particularly preferred aspect, the subject is a subject suffering from metastatic cancer and undergoing a palliative radiotherapy, a subject suffering from metastatic cancer for whom radiotherapy has been abandoned, or a subject suffering from a cancer which is not treated by radiotherapy, and the fractionated radiotherapy is selected from 1 fraction of 6 Gy (total: 6 Gy), 2 fractions of 6 Gy (total: 12 Gy), 3 fractions of 6 Gy (total: 18 Gy), 4 fractions of 6 Gy (total: 24 Gy), 5 fractions of 6 Gy (total: 30 Gy), 1 fraction of 7 Gy (total: 7 Gy), 2 fractions of 7 Gy (total: 14 Gy), 3 fractions of 7 Gy (total: 21 Gy), 4 fractions of 7 Gy (total: 28 Gy), 1 fraction of 8 Gy (total: 8 Gy), 2 fractions of 8 Gy (total: 16 Gy), 3 fractions of 8 Gy (total: 24 Gy), 4 fractions of 8 Gy (total: 32 Gy), 1 fraction of 9 Gy (total: 9 Gy), 2 fractions of 9 Gy (total: 18 Gy), 3 fractions of 9 Gy (total: 27 Gy), 1 fraction of 10 Gy (total: 10 Gy), 2 fractions of 10 Gy (total: 20 Gy), 3 fractions of 10 Gy (total: 30 Gy), 1 fraction of 15 Gy (total: 15 Gy), 2 fractions of 15 Gy (total: 30 Gy), 1 fraction of 20 Gy (total: 20 Gy), 2 fractions of 20 Gy (total: 40 Gy), 1 fraction of 25 Gy (total: 25 Gy) and 1 fraction of 30 Gy (total: 30 Gy).

Nanoparticle

The nanoparticle used in the context of the invention advantageously consists in a material having a density of at least 7 g/cm$^3$ and an atomic number (Z) of at least 25. The nanoparticle or aggregate of nanoparticles is covered with a biocompatible coating allowing the nanoparticle stability between pH 6.5 and 7.5 in a physiological fluid.

In the spirit of the invention, the term "nanoparticle" refers to a product, in particular a synthetic product, with a size in the nanometer range, typically between 1 nm and 500 nm.

The term "aggregate of nanoparticles" refers to an assemblage of nanoparticles strongly, typically covalently, bound to each other.

Transmission electron microscopy (TEM) can be used to measure the size of the nanoparticle. As well, dynamic light scattering (DLS) can be used to measure the hydrodynamic diameter of nanoparticles in solution. These two methods may further be used one after each other to compare size measures and confirm said size. A preferred method is DLS (Ref International Standard ISO22412 Particle Size Analysis-Dynamic Light Scattering, International Organisation for Standardisation (ISO) 2008). The largest dimension of a nanoparticle as herein defined is typically between about 4 nm and about 250 nm, preferably between about 4 nm or 10 nm and about 100 nm or about 200 nm, even more preferably between about 20 nm and about 150 nm.

As the shape of the particle can influence its "biocompatibility", particle having a quite homogeneous shape is preferred. For pharmacokinetic reasons, nanoparticles being essentially spherical, round or ovoid in shape are thus preferred. Such a shape also favors the nanoparticle interaction with or uptake by cells. Spherical or round shape is particularly preferred.

Typically, the largest dimension is the diameter of a nanoparticle of round or spherical shape, or the longest length of a nanoparticle of ovoid or oval shape.

The inorganic material of the nanoparticle present in the composition preferably has a theoretical (bulk) density of at least 7 and may be selected from any material exhibiting this property and identified in the table from Physical Constants of Inorganic Compounds appearing on page 4-43 in Handbook of Chemistry and Physics (David R. Lide Editor-In-Chief, 88$^{th}$ Edition 2007-2008).

The inorganic material constituting the nanoparticle is preferably a material having an effective atomic number ($Z_{eff}$) of at least 25, preferably at least 40 or 41, more preferably at least 50 or 51, more preferably at least 60, 61, 62 or even 63.

Effective atomic number is a term that is similar to atomic number but is used for compounds (e.g. water) and mixtures of different materials (such as tissue and bone) rather than for atoms. Effective atomic number calculates the average atomic number for a compound or mixture of materials. It is abbreviated $Z_{eff}$.

The effective atomic number is calculated by taking the fractional proportion of each atom in the compound and multiplying that by the atomic number of the atom. The formula for the effective atomic number, $Z_{eff}$, is as follows:

$$Z_{eff} = \sqrt[2.94]{f_1 \times (Z_1)^{2.94} + f_2 \times (Z_2)^{2.94} + f_3 \times (Z_3)^{2.94} + \ldots}$$

where $f_n$ is the fraction of the total number of electrons associated with each element, and $Z_n$ is the atomic number of each element.

The atomic number (also known as the proton number) is the number of protons found in the nucleus of an atom. It is traditionally represented by the symbol Z. The atomic number uniquely identifies a chemical element. In an atom of neutral charge, atomic number is equal to the number of electrons. An example is that of water ($H_2O$) which is made up of two hydrogen atoms (Z=1) and one oxygen atom (Z=8). The total number of electrons is 1+1+8=10. The fraction of electrons corresponding to the two hydrogens is $2/10$ and the fraction of electrons corresponding to the unique oxygen is ($8/10$). $Z_{eff}$ of water is therefore:

$$Z_{eff} = \sqrt[2.94]{0.2 \times 1^{2.94} + 0.8 \times 8^{2.94}} = 7.42$$

$Z_{eff}$ participate to the incoming radiations absorption capacity of nanoparticles.

The inorganic material constituting the nanoparticle is typically selected from an oxide, a metal, a sulfide and any mixture thereof.

When the inorganic material constituting the nanoparticle is an oxide, this oxide is advantageously selected from Cerium (IV) oxide ($CeO_2$), Neodynium (III) oxide ($Nd_2O_3$), Samarium (III) oxide ($Sm_2O_3$), Europium (III) oxide ($Eu2O_3$), Gadolinium (III) oxide ($Gd_2O_3$), Terbium (III) oxide ($Tb_2O_3$), Dysprosium (III) oxide ($Dy_2O_3$), Holmium oxide ($Ho_2O_3$), Erbium oxide ($Er_2O_3$), Thullium (III) oxide ($Tm_2O_3$), Ytterbium oxide ($Yb_2O_3$), Lutetium oxide ($Iu_2O_3$), Hafnium (IV) oxide ($HfO_2$), Tantalum (V) oxide ($Ta_2O_5$), Rhenium (IV) oxide ($ReO_2$), Bismuth (III) oxide ($Bi_2O_3$). In the context of the present invention, a mixture of inorganic oxides can also be used to prepare the nanoparticle of the invention.

When the inorganic material constituting the nanoparticle is a metal, this metal is advantageously selected from gold (Au), silver (Ag), platinum (Pt), palladium (Pd), tin (Sn), tantalum (Ta), ytterbium (Yb), zirconium (Zr), hafnium (Hf), terbium (Tb), thulium (Tm), cerium (Ce), dysprosium (Dy), erbium (Er), europium (Eu), holmium (Ho), iron (Fe), lanthanum (La), neodymium (Nd), praseodymium (Pr), lutetium (Lu). In the context of the present invention, mixture of metals is also possible. In the context of the present invention, a mixture of an inorganic oxide and of a metal can also be used to prepare the nanoparticle of the invention.

When the inorganic material constituting the nanoparticle is a sulfide, this sulfide is preferably silver sulfide ($Ag_2S$).

In a preferred embodiment, the nanoparticle used in the context of the present invention to prepare a composition of interest can be coated with a biocompatible material selected from an agent exhibiting stealth property. Indeed, when the nanoparticles of the present invention are administered to a subject via the intravenous (IV) route, a biocompatible coating with a material selected from an agent exhibiting stealth property is particularly advantageous to optimize the biodistribution of the nanoparticles. Said coating is responsible for the so called "stealth property" of the nanoparticle.

Agent exhibiting stealth properties may be an agent displaying a steric group. Such a group may be selected for example from polyethylene glycol (PEG); polyethylenoxide; polyvinylalcohol; polyacrylate; polyacrylamide (poly (N-isopropylacrylamide)); polycarbamide; a biopolymer; a polysaccharide such as dextran, xylan and cellulose; collagen; a zwitterionic compound such as polysulfobetain; etc.

In another preferred embodiment, the nanoparticles can be coated with a biocompatible material selected from an agent allowing interaction with a biological target. Such an agent can typically bring a positive or a negative charge on the nanoparticle's surface. This charge can be determined by zeta potential measurements, typically performed on nanoparticles suspensions the concentration of which vary between 0.2 and 10 g/L, the nanoparticles being suspended in an aqueous medium with a pH comprised between 6 and 8.

An agent forming a positive charge on the nanoparticle surface can be for example aminopropyltriethoxisilane or polylysine. An agent forming a negative charge on the nanoparticle surface can be for example a phosphate (for example a polyphosphate, a metaphosphate, a pyrophosphate, etc.), a carboxylate (for example citrate or dicarboxylic acid, in particular succinic acid) or a sulphate.

A full biocompatible coating of the nanoparticle or aggregate may be advantageous, in particular in the intravenous (IV) context, in order to avoid interaction of the particle surface with any recognition element (macrophage, opsonins, etc.). The "full coating" implies the presence of a very high compactness of biocompatible molecules able to create at least a complete monolayer on the surface of the particle.

The biocompatible coating allows in particular the nanoparticle stability in a fluid, such as a physiological fluid (blood, plasma, serum, etc.) or any isotonic media or physiologic medium required for a pharmaceutical administration.

Stability may be confirmed by dry extract quantification using a drying oven and measured on a nanoparticle suspension prior and after filtration, typically on a 0.22 or 0.45 μm filter.

Advantageously, the coating preserves the integrity of the particle in vivo, ensures or improves the biocompatibility thereof, and facilitates an optional functionalization thereof (for example with spacer molecules, biocompatible polymers, targeting agents, proteins, etc.).

A particular nanoparticle according to the present invention can further comprise a targeting agent allowing its interaction with a recognition element present on the target cell. Such a targeting agent typically acts once the nanoparticles are accumulated on the target site. The targeting agent can be any biological or chemical structure displaying affinity for molecules present in the human or animal body. For instance it can be a peptide, oligopeptide or polypeptide, a protein, a nucleic acid (DNA, RNA, SiRNA, tRNA, miRNA, etc.), a hormone, a vitamin, an enzyme, the ligand of a molecule expressed by a pathological cell, in particular the ligand of a tumor antigen, hormone receptor, cytokine receptor or growth factor receptor. Said targeting agents can be selected for example in the group consisting in LHRH, EGF, a folate, anti-B-FN antibody, E-selectin/P-selectin, anti-IL-2R☐ antibody, GHRH, etc.

Composition

Inventors also herein describe a therapeutic composition, typically a vaccine composition, for use in a subject suffering from cancer as herein defined, preferably from a metastatic cancer or from a liquid cancer, in the context of radiotherapy, typically of a fractionated radiotherapy as herein defined, wherein the composition comprises (i) a nanoparticle or aggregate of nanoparticles, each nanoparticle consisting in a material having a density of at least 7 g/cm$^3$ and an atomic number (Z) of at least 25, and each nanoparticle or aggregate of nanoparticles being covered with a biocompatible coating allowing the nanoparticle stability between pH 6.5 and 7.5 in a physiological fluid, preferably together with (ii) a pharmaceutically acceptable carrier or vehicle.

In a particular embodiment, a vaccine composition is herein described which comprises a nanoparticle and/or aggregate of nanoparticles for use for treating cancer in a subject suffering from metastatic cancer and undergoing a palliative radiotherapy, in a subject suffering from metastatic cancer for whom (curative) radiotherapy has been abandoned, in a subject suffering from a cancer which is not treated by radiotherapy, or in a subject suffering from a liquid cancer, wherein the treatment comprises exposing the subject to a fractionated radiotherapy comprising at least one irradiation step wherein the ionizing radiations dose ranges from 1.8 to 30 Gray (Gy), preferably 1.8 to 20 Gray (Gy), and wherein each nanoparticle consists in a material having a density of at least 7 g/cm$^3$ and an atomic number (Z) of at least 25 and each nanoparticle or aggregate of nanoparticles is covered with a biocompatible coating allowing the nanoparticle stability between pH 6.5 and 7.5 in a physiological fluid. The composition may comprise in addition to the nanoparticle and/or aggregate of nanoparticles a pharmaceutically acceptable carrier or vehicle.

The pharmaceutically acceptable carrier or vehicle can be any classical support for the skilled person, such as for example a saline, isotonic, sterile, buffered solution, a non-aqueous vehicle solution and the like. A typical carrier is a isotonic media or physiological media comprising NaCl, PBS and/or Glucose. The carrier can for example comprise glucose (5%) or dextrose (5%) and/or NaCl (0.9%).

The composition can also comprise stabilizers, sweeteners, surfactants, polymers and the like.

The composition can be in the form of a solid, liquid (particles in suspension), aerosol, gel, paste, and the like. Preferred compositions are in a liquid or a gel form. Particularly preferred compositions are in liquid form.

It can be formulated for example as ampoule, syringe, aerosol, bottle, vial, tablet, capsule, by using techniques of pharmaceutical formulation known by the skill person.

Generally, the composition, in liquid or gel form, comprise between about 0.05 g/L and about 450 g/L of nanoparticles or aggregates of nanoparticles, between about 0.05 g/L and about 250 g/L of nanoparticles, preferably at least about 10 g/L, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 85 g/L, 90 g/L, 95 g/L, 100 g/L, 150 g/L, 200 g/L, 250 g/L, 300 g/L, 350 g/L, or 400 g/L of nanoparticles.

The concentration of nanoparticles in the composition can be measured by dry extract. A dry extract is ideally measured following a drying step of the suspension comprising the nanoparticles in a drying oven.

In a particular embodiment, the composition further comprises at least one immunotherapeutic agent and optionally an additional therapeutic agent for treating cancer.

The terms "immunotherapeutic agent" herein designates typically any molecule, drug, cell or cell-based vaccine, oncolytic virus, DNA-based vaccine, peptide-based vaccine, toll-like receptor (TLR) agonist, vesicle derived from a cell as well as any combination thereof capable of boosting the immune system of a subject and recognized as such by the skilled person.

The molecule or drug can for example be selected from a monoclonal antibody, a cytokine, and a combination thereof.

The drug can typically be an indoleamine 2,3-dioxygenase (IDO) inhibitor such as 1-methyl-D-tryptophan.

In a preferred embodiment, the monoclonal antibody inhibits the cytotoxic T-lymphocyte-associated antigen 4 (CTLA-4) molecule or the interaction between programmed cell death protein 1 (PD-1) and its ligands. The monoclonocal antibody is advantageously selected from anti-CTLA-4, anti-PD-1, anti-programmed cell death ligand 1 (PD-L1), anti-programmed cell death 1 ligand 2 (PD-L2). The monoclonal antibody can for example be selected from ipilimumab, tremelimumab, nivolumab, prembolizumab, pidilizumab and lambrolizumab.

In another preferred embodiment, the monoclonal antibody enhances CD27 cluster of differentiation 27 (CD27) signaling, CD137 signaling, tumor necrosis factor receptor superfamily member 4 (also known as OX-40) signaling, glucocorticoid-induced tumor necrosis factor receptor-related (GITR) signaling and/or WWII major histocompatibility complex class II (MHII) signaling, and/or activate CD40. The monoclonal antibody can for example be selected from dacetuzumab, Lucatumumab, and urelumab.

In a further embodiment, the monoclonal antibody inhibits transforming growth factor-β (TGF-β) signaling or killer cell immunoglobulin-like receptors (KIR) signaling. The monoclonal antibody can for example be selected from fresolimumab and lirilumab.

The cytokine can be advantageously selected from the granulocyte-macrophage colony stimulating factor (GM-CSF), a fms-related tyrosine kinase 3 ligand (FLT3L), b, interferon-alpha (IFN-α), interferon-alpha-2-beta (IFN-α213), interferon gamma (IFNγ), interleukin-2 (IL2), interleukin-7 (IL-7), interleukin-10 (IL-10) and interleukin-15 (IL-15).

In another preferred embodiment, the monoclonal antibody enhances CD27 signaling, CD137 signaling, OX-40 signaling, GITR signaling and/or MHCII signaling, and/or activate CD40. The monoclonal antibody can for example be selected from dacetuzumab, Lucatumumab, and urelumab.

In another preferred embodiment, the immunotherapeutic agent is an immunocytokine, for example the immunocytokine L19-IL2 (Nicolle H. Rekers Radiotherapy and Oncology 2015).

The cell as used as an immunotherapeutic agent is typically an immune cell presenting or sensitized to a tumor antigen, preferably a tumor antigen specific of the cancer to be treated, such as a dendritic cell or a T-cell; a cell secreting an immunogenic molecule; or a dead tumor cell or a dying tumor cell undergoing an immunogenic cell death, i.e. a cell expressing CRT and/or producing HMGB1 and/or producing ATP in a ICD typical amount, for example a dying or dead-tumor cell which has been exposed to radiotherapy. The cell can be an autologous cell or an allogeneic cell. The cell is preferably an autologous cell isolated from the subject to be treated. The dead- or dying-tumor cell can be a tumor mature cell or a tumor stem cell.

The toll-like receptor agonist is advantageously selected from a TLR 2/4 agonist, a TLR 7 agonist, a TLR 7/8 agonist and a TLR 9 agonist. The toll-like receptor agonist can for example be selected from imiquimod, *bacillus* Calmette-Guérin and monophosphoryl lipid A.

A preferred combination of immunotherapeutic agents can be for example selected from a cytokine, a monoclonal antibody, a Toll-like receptor agonist and a peptide-based vaccine.

The terms "therapeutic agent for treating cancer" herein typically designates an agent used in a conventional treatment of cancer such a biological compound, a small molecule targeted therapeutic, or a cytotoxic compound.

A biological compound is for instance an antibody, preferably a monoclonal antibody ("mAb") such as Alemtuzumab, Brentuximab Vedotin, Catumaxoma, Denosumab, Gemtuzumab ozogamicin, Ibritumomab tiuxetan, Pertuzumab, Ofatumumab, bevacizumab, rituximab, trastuzumab, cetuximab, panatimumab or tositumomab.

A small molecule targeted therapeutic generally inhibits enzymatic domains on mutated, overexpressed, or otherwise critical protein (potential target in the context of cancer treatment) within the malignant cells. Some therapeutic agents include those that target cell division (for example an aurora-kinase inhibitor or a cyclin-dependent-kinase inhibitor), as well as other biological mechanisms such as protein turnover and chromatin modification (for example a histone-deacetylase inhibitor). Small molecules targeted therapeutics can for example be selected from imatinib, rapamycin, gefitinib, erlotinib, sorafenib, sunitinib, nilotinib, dasatinib, lapatinib, bortezomib and atorvastatin, etc. A cytotoxic compound is for example a DNA-modifying agent such as an anthracyclin (such as dexamethasone, daunorubicin, idarubicin or methotrexate) or an antimitotic agent (spindle poison such as vincristine or vinblastine); a taxane such as docetaxel, larotaxel, cabazitaxel, paclitaxel (PG-paclitaxel and DHA-paclitaxel), ortataxel, tesetaxel or taxoprexin; gemcitabine; etoposide; mitomycine C; an alkylating agent (for example melphalan or temozolomide); a platin based component such as oxaliplatin or carboplatin; a TLR (Toll-like receptor)-3 ligand; and a prodrug.

The prodrug (for instance capecitabine or irinotecan) is metabolized in its active form in vivo to produce its expected therapeutic effect.

Other typical cytotoxic compounds are typically selected from chemotherapeutic agents as herein described or as known by the skilled oncologist.

The herein described vaccine composition comprising at least one immunotherapeutic agent, possibly in combination with a least one therapeutic agent for treating cancer, can be administered to the subject to be treated either simultaneously or separately from the nanoparticles or aggregates of nanoparticles as herein described.

Kit

Inventors also herein describe a vaccine kit comprising (i) a nanoparticle or aggregate of nanoparticles consisting in a material having a density of at least 7 g/cm$^3$ and an atomic number (Z) of at least 25, each nanoparticle or aggregate of nanoparticles being covered with a biocompatible coating allowing the nanoparticle stability between pH 6.5 and 7.5 in a physiological fluid, or a vaccine composition as herein described, preferably together with (ii) at least one immunotherapeutic agent and/or therapeutic agent for treating cancer as herein described, and optionally (iii) a leaflet providing instructions to perform the vaccination in the context of radiotherapy.

Protocol

The nanoparticles or aggregates of nanoparticles as herein described or the composition comprising such nanoparticles or aggregates of nanoparticles are advantageously contacted with the cancer cells before radiotherapy, typically the fractionated radiotherapy, is applied. The contact between nanoparticles and cancer cells can be performed ex vivo following biopsy or blood sampling, or in vivo through administration to the subject to be treated either systemically or directly into the tumor, tumor bed (after tumor resection by surgery) or tumor metastase(s).

When administered in vivo, the nanoparticles of the invention can be administered to the subject using different possible routes such as local [intra-tumoral (IT), intra-arterial (IA)], subcutaneous, intra venous (IV), intra-dermic, airways (inhalation), intra peritoneal, intra muscular, intra-articular, intra-thecal, intra-ocular or oral route (per os), preferably using IT, IV or IA.

Repeated injections or administrations of nanoparticles can be performed, when appropriate.

In a particular embodiment, the nanoparticle or aggregate of nanoparticles is advantageously administered to the subject to be treated together with at least one immunotherapeutic agent. The nanoparticle or aggregate of nanoparticles, or the composition comprising such nanoparticle or aggregate of nanoparticles, and the at least one immunotherapeutic agent can be administered to the subject either simultaneously or separately.

In a particular embodiment, when the cancer is a metastatic cancer and/or is a cancer which is not (conventionally) treated by radiotherapy, the at least one irradiation step is typically applied in vivo on one, at most two, tumor sites of the metastatic cancer comprising the nanoparticles or aggregates of nanoparticles. Thanks to the nanoparticles or aggregates of nanoparticles used as a vaccine the anti-cancer effect of radiotherapy can be observed outside of the irradiated area or site due to the efficient mobilization of the subject's immune system.

Typically, inventors herein demonstrate that a marked increase of HMGB1 released from dying cancer cell is observed with the nanoparticles or aggregates of nanoparticles of the invention exposed to ionizing radiations when compared to radiation alone in both radiosensitive HCT 116 (human colorectal cancer cell line) and radioresistants 42 MG BA (human glioblastoma cell line) and PANC-1 (human pancreas cancer cell line), using a single dose of radiations. Moreover, a marked increase of ATP secretion from dying cancer cell is observed with the nanoparticles or aggregates of nanoparticles of the invention exposed to ionizing radiations when compared to radiation alone in HCT 116 cancer cell line.

These DAMPs are an indication of the immunogenic cell death of cancer cells, and the nanoparticles or aggregates of nanoparticles of the present invention when exposed to radiations therapy are able to amplify their secretion and release.

In addition, results of the vaccination assay performed in immunocompetent mice show the ability of the nanoparticles or aggregates of nanoparticles of the invention to efficiently mobilize the immune system of the animals, preventing the apparition of tumors when animals are first vaccinated with irradiated cancer cells and then challenged 7 days after with viable cancer cells: 66% of the animals are tumor free in the group vaccinated with cancer cell treated with the nanoparticles and 6 Gy whereas only 33% of the animal are tumor free when vaccinated with cancer cells irradiated with 6 Gy alone.

These data strongly support the use of these nanoparticles or aggregates of nanoparticles as a vaccine to generate the anti-cancer effect of radiotherapy outside of the irradiated area or site due to the efficient mobilization of the subject's immune system.

In a preferred embodiment, the nanoparticle or nanoparticles' aggregate of the invention, or the composition of the invention comprising such a nanoparticle or nanoparticles' aggregate allows the alteration or destruction of metastatic cancer cells present in lung (e.g. when the primary cancer is for example a sarcoma, bladder cancer, breast cancer, colon cancer, kidney cancer or prostate cancer), liver (e.g. when the primary cancer is for example a gastrointestinal cancer, a breast cancer, a colon cancer, lung cancer or skin cancer), bone (e.g. when the primary cancer is for example a breast cancer, a prostate cancer or a lung cancer) and/or brain (e.g. when the primary cancer is for example a lung cancer, a renal cancer, a melanoma or a breast cancer).

In another particular embodiment, the at least one irradiation step is applied ex vivo on a cancer sample of the subject comprising the nanoparticles or aggregates of nanoparticles, and the ex vivo lethally irradiated cancer cells together with at least part of the associated cell supernatant from the cancer sample are at least partly readministered to the subject before any optional subsequent in vivo treatment of cancer in said subject.

Cell supernatant from the irradiated cancer sample typically comprises immunogenic molecules such as HMGB1, ATP, various chaperones of the heat shock protein (HSP) family, notably the heat shock 70 kDa protein (HSP70) and the heat shock 90 kDa protein (HSP90), immunostimulatory cytokines like interferon α (IFNα), sphingomyelin metabolites, product from the breakdown of the extracellular matrix, etc. In the context of the present invention, the enhanced release of immunogenic molecules in the cell supernatant from the irradiated cancer sample comprising the nanoparticles or aggregate of nanoparticles, when compared to irradiated cancer sample with absence of nanoparticles or aggregate of nanoparticles (see example 4), is capable of further amplifying the anti-cancer treatment.

Readministration into the subject to be treated is typically performed through subcutaneous or intradermal injection.

When the cancer is a liquid cancer, the at least one irradiation step is typically applied ex vivo on a liquid cancer sample of the subject comprising the nanoparticles or aggregates of nanoparticles, and the irradiated liquid cancer sample is at least partly readministered to the subject before any optional subsequent in vivo treatment of cancer in said subject.

Readministration into the subject to be treated can be performed through subcutaneous or intradermal injection. It can also be performed through intraarterial (IA), intravenous (IV) or intraperitoneal (IP) injection.

The liquid cancer sample is typically a blood sample or the whole blood volume of the subject to be treated. When the whole blood volume of the subject is to be irradiated, irradiation can be performed ex vivo during an extra corporeal circulation protocol, the irradiated whole blood volume being completely readministered to the subject.

Of interest, Y. Suzuki et al. (2012) reported that tumor antigen-specific T-cell responses were observed in 38% of patients with esophageal squamous cell carcinoma (ESCC) after chemoradiotherapy and that these responses were coexisting with an elevated HMGB1 concentration in the serum of these patients. HMGB1 within tumor microenvironment was significantly upregulated in patients with ESCC with preoperative chemoradiotherapy, but not in those without chemoradiotherapy, and the degree of HMGB1 positively correlated with patient survival.

In a preferred embodiment, the ex vivo lethally irradiated cancer cells or the irradiated liquid cancer sample is at least partly readministered to the subject together with at least one additional immunotherapeutic agent and/or therapeutic agent for treating cancer as herein described.

The ex vivo lethally irradiated cancer cells or the irradiated liquid cancer sample and the least one additional immunotherapeutic agent and/or the at least therapeutic agent for treating cancer can be administered to the subject either simultaneously or separately.

Other aspects and advantages of the invention will become apparent in the following examples, which are given for purposes of illustration and not by way of limitation.

EXPERIMENTAL SECTION

Example 1

Functionalized Hafnium Oxide ($HfO_2$) Nanoparticles Synthesis and Characterization A Tetramethylammonium hydroxide (TMAOH) solution is added to 40 g of $HfCl_4$ solution. Addition of TMAOH solution is performed until the pH of the final suspension reaches a pH comprised between 7 and 13. A white precipitate is obtained.

The precipitate is further transferred in an autoclave and heated at a temperature comprised between 120° C. and 300° C. to perform crystallization. After cooling, the suspension is washed with de-ionized water.

A peptization step, is performed in order to get a stable suspension of nanoparticles or nanoparticle aggregates.

Suspension of Sodium hexametaphosphate is then added to the peptized solution (the amount of sodium hexametaphosphate added being below LD50/5) and the pH of the suspension is adjusted to a pH comprised between 6.5 and 7.5.

For in vitro experiments a sterilization step is performed at this stage for example using a 0.22 μm filter.

For in vivo experiments, a formulation step using glucose 5% can be performed before or after the sterilization step.

The following table presents the main characteristics of the suspension of biocompatible nanoparticles or nanoparticle aggregates thus obtained.

| Density | Morphology | Specific surface area (SS) in m²/g | Mean hydrodynamic diameter (Φ) in nm |
|---|---|---|---|
| 8.3 | Spherical in shape | 20 < SS < 60 | 15 < Φ < 200 |

Example 2

Gold Nanoparticles Synthesis and Physico-Chemical Characterization of Gold Nanoparticles of Different Sizes Gold nanoparticles are obtained by reduction of gold chloride with sodium citrate in aqueous solution. Protocol was adapted from G. Frens Nature Physical Science 241 (1973) 21.

In a typical experiment, $HAuCl_4$ solution is heated to boiling. Subsequently, sodium citrate solution is added. The resulting solution is maintained under boiling for an additional period of 5 minutes.

The nanoparticle size is adjusted from 15 up to 105 nm by carefully modifying the citrate versus gold precursor ratio (cf. Table 1).

The as prepared gold nanoparticles suspensions are then concentrated using an ultrafiltration device (Amicon stirred cell model 8400 from Millipore) with a 30 kDa cellulose membrane.

The resulting suspensions are ultimately filtered through a 0.22 μm cutoff membrane filter (PES membrane from Millipore) under laminar hood and stored at 4° C.

Particle size is determined using Transmission Electronic Microscopy (TEM) by counting more than 200 particles, taking the longest nanoparticle dimension for size measurement.

TABLE 1

| Samples | Particle size (nm) | Synthesis Citrate | $HAuCl_4$ |
|---|---|---|---|
| Gold-15 | 15 ± 2 (1σ) | 20 mL 30 mM | 500 mL 0.25 mM |
| Gold-30 | 32 ± 10 (1σ) | 7.5 mL 40 mM | 500 mL 0.25 mM |
| Gold-60 | 60 ± 10 (1σ) | 2 mL 85 mM | 500 mL 0.25 mM |
| Gold-80 | 80 ± 10 (1σ) | 1.2 mL 43 mM | 200 mL 0.30 mM |
| Gold-105 | 105 ± 25 (1σ) | 1.2 mL 39 mM | 200 mL 0.33 mM |

Example 3

Nanoparticles Suspension Comprising a Gold Material at Least Partially Covered with Hafnium Oxide Material A Tetramethylammonium hydroxide (TMAOH) solution is added to hafnium chloride ($HfCl_4$) solution. Addition of TMAOH solution is performed until the pH of the final suspension reaches a pH comprised between 7 and 13. A white precipitate is obtained.

Gold particles suspension from example 2 is slowly added to the white precipitate under vigorous mixing.

The resulting precipitate is further transferred in an autoclave and heated at a temperature comprised between 100° C. and 300° C. After cooling, the suspension is washed with water.

A peptization step is performed in order to get a stable suspension of nanoparticles comprising gold material at least partly embedded in hafnium oxide material.

Suspension of sodium hexametaphosphate is then added to the peptized solution and the pH of the suspension is adjusted to a pH comprised between 6 and 8.

Example 4

HMGB1 Release from Dying Cancer Cell

HMGB1 release from dying cancer cell was studied using the 42 MG BA human glioblastoma cell line. The cell line 42-MG-BA was purchased from the Deutsche Sammlung von Mikroorganismen und Zelkulturen GmbH German Collection of Microorganism and Cell Cultures (Braunschweig, Germany).

Cells were dispersed in T25 flasks within the range of $1.5 \times 10^6$ to $2 \times 10^6$ cells/flasks. When cells were attached to the plate, $HfO_2$ nanoparticle suspension from example 1 at a concentration equal to 400 μM was added overnight (12 h-15 h) to the cells before delivering the radiation dose. The cells were cultured with antibiotics (Penistrepto).

A single X-ray irradiation dose of 5 Gy or 10 Gy was delivered at a dose rate of 1.26 Gy min$^{-1}$ using X-Ray generator (200 kV, 15 mA, 0.2 mm Copper filtration).

The cells were cultured for 96 hours at 37° C. under a 5% $CO_2$ humidified atmosphere. After 96 hours, the cell supernatant was collected and concentrated using centricon.

HMGB1 was quantified in the concentrated cell supernatants using enzyme-linked immunosorbent assay (ELISA) kit specific for human HMGB1.

Figure 1:
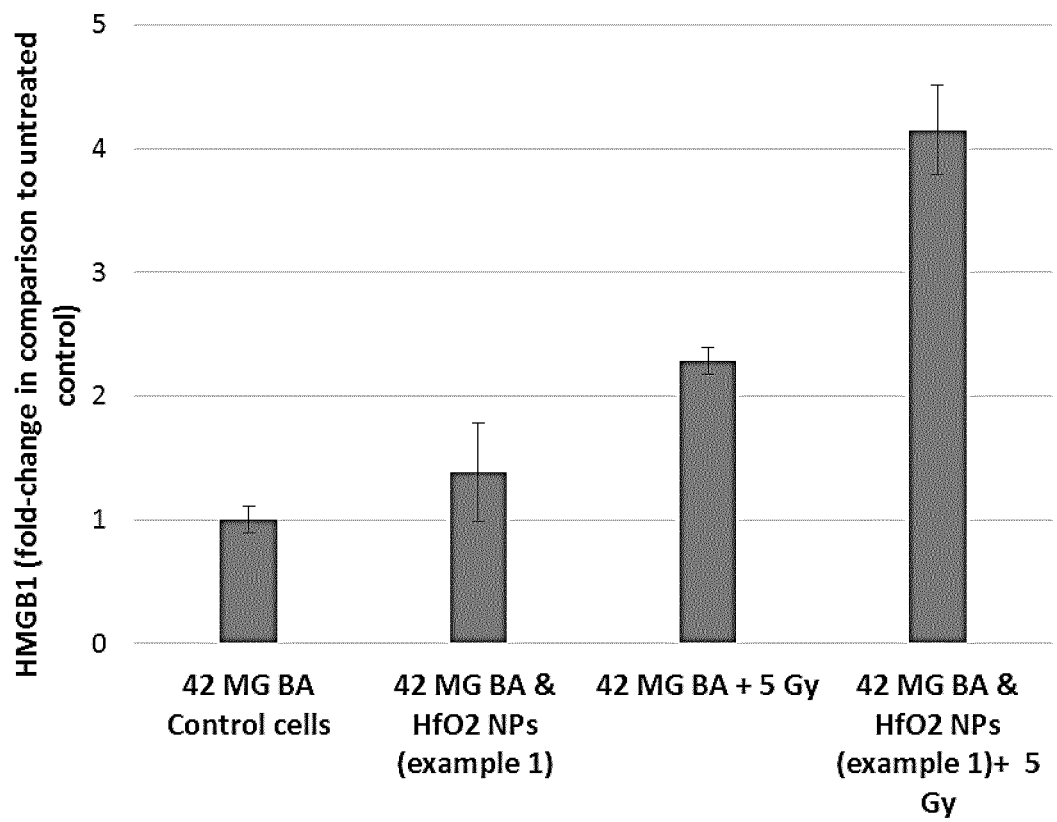
FIG. 1: HMGB1 released in the concentrated cell supernatant from cells treated or not with HfO$_2$ nanoparticles (NPs) suspension from example 1 and exposed or not to radiotherapy (5 Gy delivered in a single fraction) is reported as fold-change in comparison to untreated control.

FIG. 1 presents HMGB1 released from dying cancer cells. The HMGB1 released in the concentrated cell supernatant from cells treated or not with $HfO_2$ nanoparticle suspension from example 1 and exposed or not to radiotherapy (5 Gy delivered in 1 fraction) is reported as fold-change in comparison to untreated control (i.e. the 42 MG BA cell line without irradiation).

Figure 2:
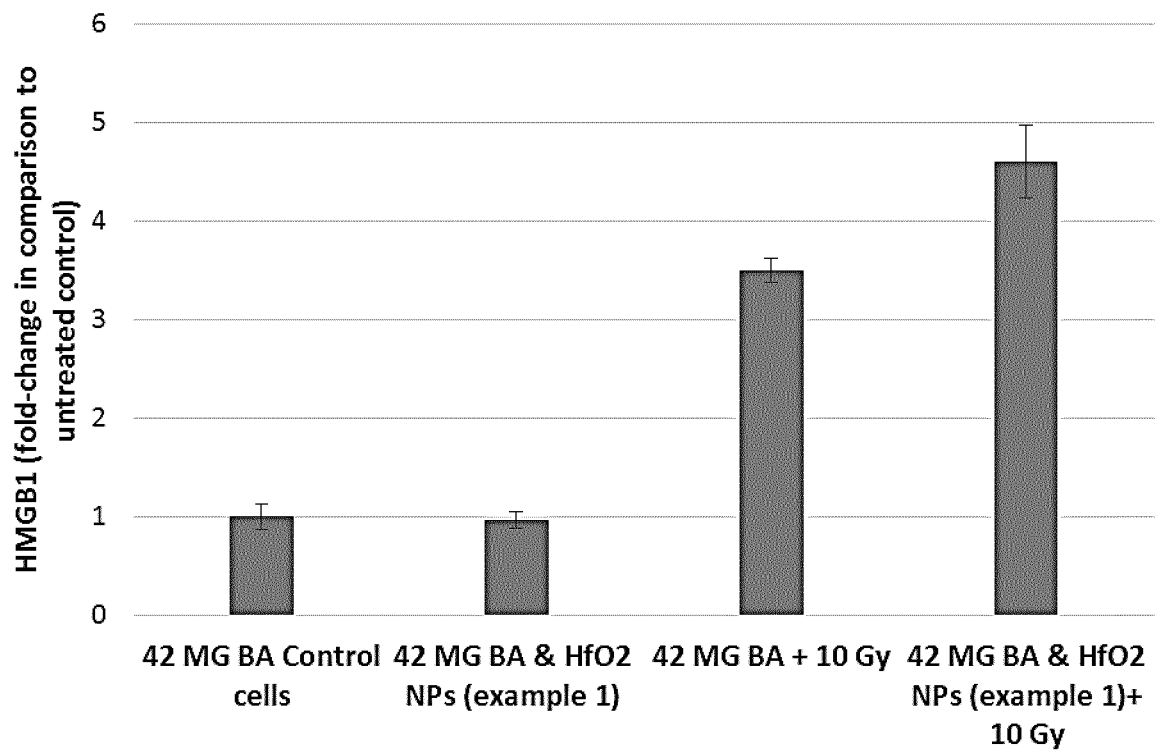
FIG. 2: HMGB1 released in the concentrated cell supernatant from cells treated or not with HfO$_2$ nanoparticles (NPs) suspension from example 1 and exposed or not to radiotherapy (10 Gy delivered in a single fraction) is reported as fold-change in comparison to untreated control.

FIG. 2 presents HMGB1 released from dying cancer cells. The HMGB1 released in the concentrated cell supernatant from cells treated or not with $HfO_2$ nanoparticle suspension from example 1 and exposed or not to radiotherapy (10 Gy delivered in 1 fraction) is reported as fold-change in comparison to untreated control (i.e. the 42 MG BA cell line without irradiation).

Conclusion

A marked increase of HMGB1 released from dying cancer cells is observed in the concentrated cell supernatant from cells treated with hafnium oxide nanoparticles from example 1 when exposed to a single irradiation dose of 5 Gy or 10 Gy, when compared to radiation alone. These results support the rational for using these nanoparticles or aggregates of nanoparticles as a therapeutic vaccine in the context of radiotherapy.

Example 5

HMGB1 Release from Dying Cancer Cells Across Cell Lines

HMGB1 release from dying cancer cell was studied using the HCT 116 human colorectal cell line, the 42 MG BA human glioblastoma cell line and the PANC-1 human pancreas cell line. The cell lines were purchased from the "American Type Culture Collection" (ATCC) (HCT 116, Catalog No. CCL-247 and PANC-1, Catalog No. CRL-1469) or from the "Deutsche Sammlung von Mikroorganismen und Zellkulturen" (DSMZ) (42 MG BA, Catalog No. ACC 431).

Cells were dispersed in T25 flasks at $1.10^6$ cells/flask. When cells were attached to the plate, $HfO_2$ nanoparticles suspension from example 1 at a concentration equal to 800 µM (for HCT 116) or 400 µM, (for PANC-1 and 42 MG) was added overnight (12 h-15 h) to the cells before delivering the radiation dose. The cells were cultured with antibiotics (medium with 1% Penicillin-Streptomycin).

X-ray irradiation doses were delivered at a dose rate of 1 $Gy.min^{-1}$ using X-ray generator (320 kV, X-RAD 320). The radiation dose for each cell line is given in table 3.

TABLE 3 irradiation doses for each cell line

| Cell line         | HCT 116      | 42 MG BA       | PANC-1 |
|-------------------|--------------|----------------|--------|
| Irradiation doses | 4 Gy<br>6 Gy | 10 Gy<br>15 Gy | 8 Gy   |

HCT 116 cell line: cells were cultured 72 hours at 37° C. under a 5% $CO_2$ humidified atmosphere. After 72 hours, the cell supernatant was collected.

42 MG BA and PANC-1 cell lines: cells were cultured 96 hours at 37° C. under a 5% $CO_2$ humidified atmosphere. After 96 hours, the cell supernatant was collected and concentrated using Centricon.

HMGB1 was quantified in the cell supernatants using enzyme-linked immunosorbent assay (ELISA) kit specific for human HMGB1 (such as "HMGB1 ELISA Kit" from IBL international, Catalog No. ST51011).

Figure 3:
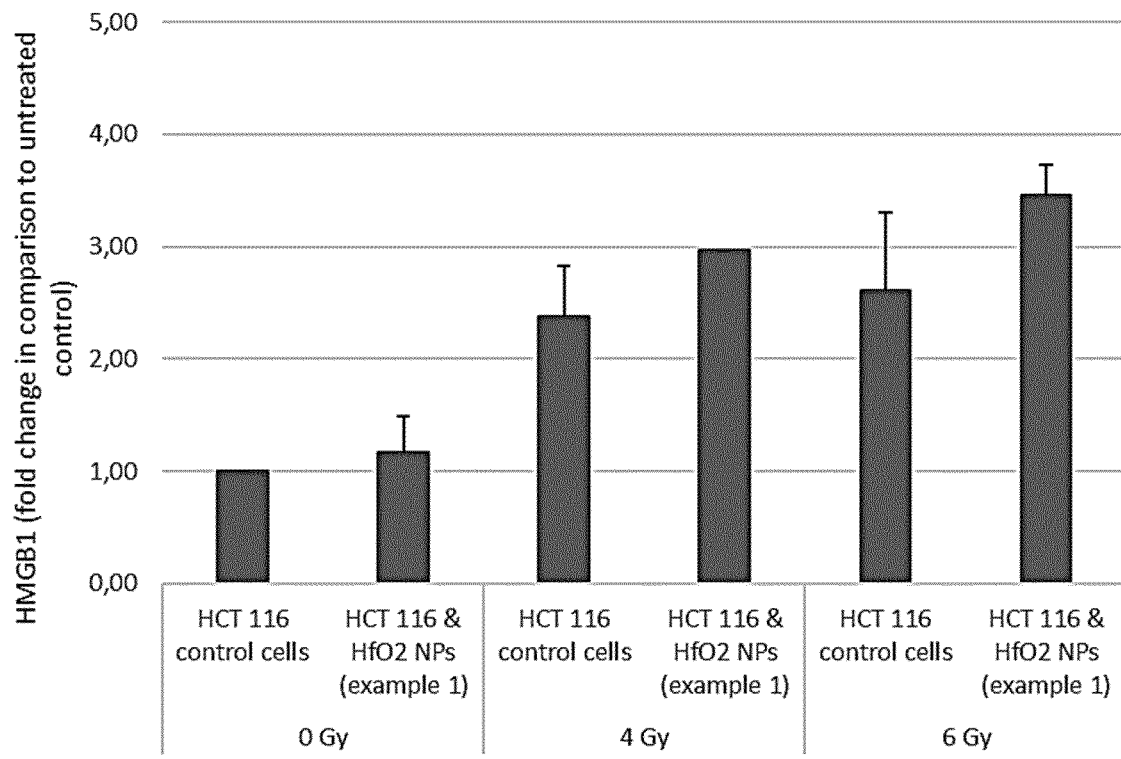
FIG. 3: HMGB1 released in the cell supernatant from cells treated or not with HfO$_2$ nanoparticles (NPs) suspension from example 1 and exposed or not to radiotherapy delivered in a single fraction is reported as fold-change in comparison to untreated control. A) the cancer cell line is the HCT 116 human colorectal cell line and the irradiation doses correspond to 4 Gy and 6 Gy; B) the cancer cell line is the 42 MG BA human glioblastoma cell line and the irradiation doses correspond to 10 Gy and 15 Gy; C) the cancer cell line is the PANC-1 human pancreas cell line and the irradiation dose corresponds to 8 Gy.
Figure 3:
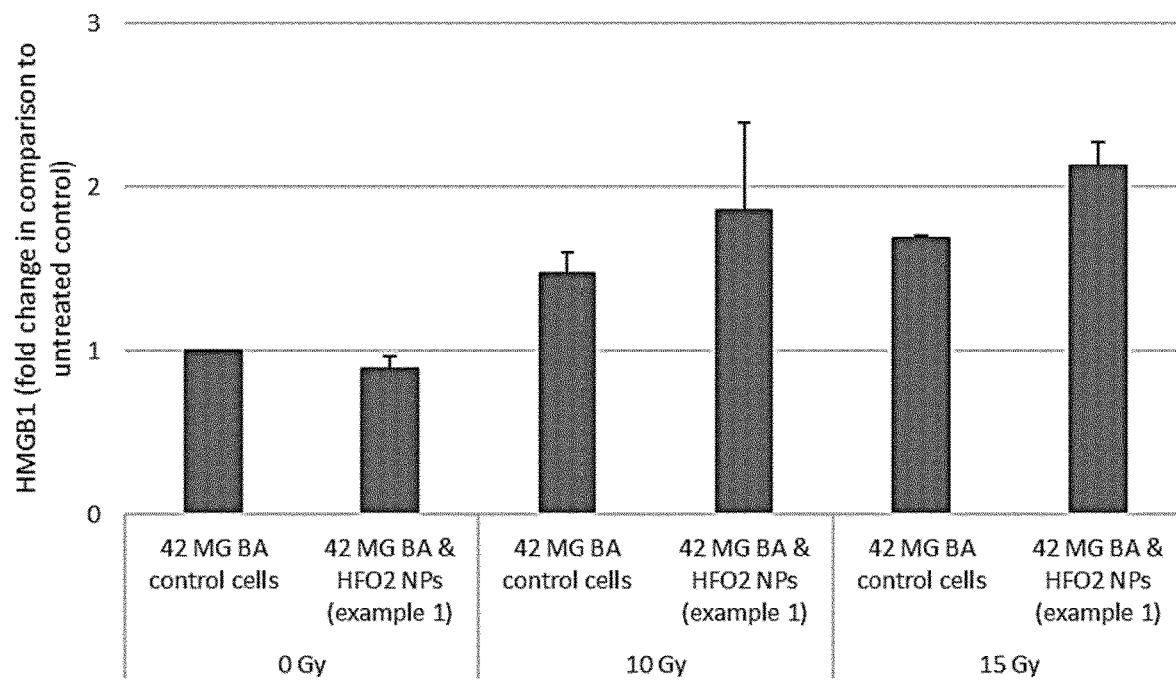
Figure 3C:
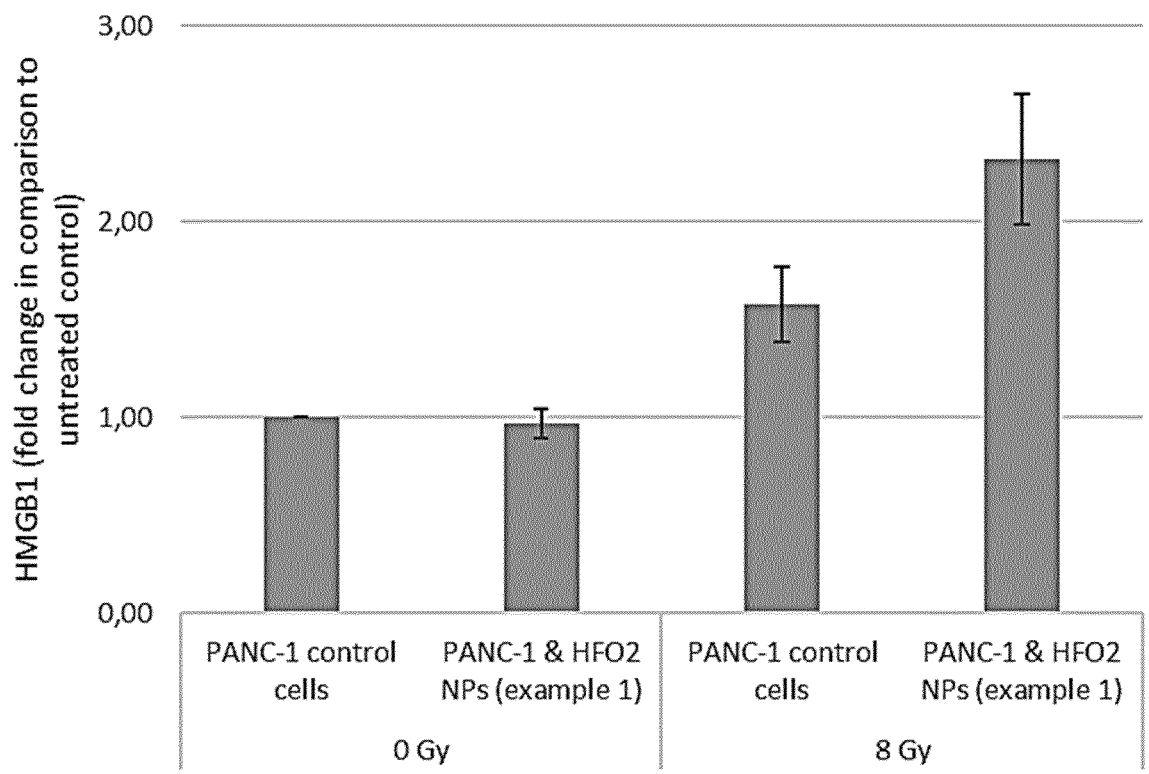

FIG. 3 presents HMGB1 released from dying cancer cells. The HMGB1 released in the cell supernatant from cells treated or not with $HfO_2$ nanoparticles suspension from example 1 and exposed or not to radiotherapy (delivered in 1 fraction) are reported as fold-change in comparison to untreated control.

FIG. 3 A represents HMGB1 released from dying HCT 116 cancer cells. Irradiation doses were equal to 4 Gy and 6 Gy. Experiments is the mean of 2 independent experiments performed in triplicate and pooled.

FIG. 3 B represents HMGB1 released from dying 42 MG BA cancer cells. Irradiation doses were equal to 10 Gy and 15 Gy. Experiments is the mean of 2 independent experiments performed in triplicate and pooled.

FIG. 3 C represents HMGB1 released from dying PANC-1 cancer cells. Irradiation dose was equal to 8 Gy. Experiments are the mean of 2 independent experiments performed in triplicate and pooled.

Conclusion

A marked increase of HMGB1 released from dying cancer cells is observed in the supernatant from cells treated with hafnium oxide nanoparticles from example 1 when exposed to a single irradiation dose, when compared to radiation alone. These results support the rationale for using these nanoparticles and/or aggregates of nanoparticles as a therapeutic vaccine in the context of radiotherapy across a large variety of cancers.

Example 6

ATP Secretion from Dying Cancer Cells

ATP secretion from dying cancer cell was studied using the HCT 116 human colorectal cancer cell line. The cell line HCT 116 was purchased from the "American Type Culture Collection" (ATCC) (HCT 116, Catalog No. CCL-247).

Cells were dispersed in T25 flasks at concentration equal to $2 \times 10^6$ cells/flask. When cells were attached to the plate, $HfO_2$ nanoparticles from example 1 at a concentration equal to 800 µM were added overnight (12 h-15 h) to cells before delivering the radiation dose. The cells were cultured with antibiotics (medium containing 1% Penicillin-Streptomycin).

A single X-ray irradiation dose of 6 Gy was delivered at a dose rate of 1 $Gy.min^{-1}$ using X-ray generator (320 kV, X-RAD 320).

The cells were cultured for 9 hours at 37° C. under a 5% $CO_2$ humidified atmosphere. After 9 hours, the cell supernatant was collected.

ATP secretion was quantified in the cell supernatants using a bioluminescence detection kit for ATP measurement (such as "ENLITEN® ATP Assay System" from Promega, Catalog. No. FF2000).

FIG. 4 presents ATP secretion from HCT 116 dying cancer cells. The ATP secretion in the cell supernatant from cells treated of not with $HfO_2$ nanoparticle suspension from example 1 and exposed or not to radiotherapy (6 Gy delivered in 1 fraction) is reported as fold-change in comparison to untreated control (i.e. the HCT 116 cell line without irradiation). Experiment is the mean of 3 independent experiments performed in triplicate and pooled.

Conclusion

A marked increase of ATP secretion from dying cancer cells is observed in the supernatant from cells treated with hafnium oxide nanoparticles from example 1 when exposed to a single irradiation dose, when compared to radiation alone. These results support the rationale for using these nanoparticles and/or aggregates of nanoparticles as a therapeutic vaccine in the context of radiotherapy.

Example 7

Vaccination Assay

As presented in the article entitled "Consensus guidelines for the detection of immunogenic cell death" (Oliver Kepp et al. Oncolmmunology 2014), the gold-standard approach to evaluate the ability of a specific stimulus to cause true ICD relies on vaccination assays. In this setting, murine cancer cells of choice are exposed in vitro to an inducer of immunogenic cell death (ICD), and eventually injected subcutaneously (s.c.) into one flank (vaccination site) of immunocompetent syngeneic mice (ideally 5-10 per group). One week later, mice are challenged with living cancer cells of the same type, which are inoculated s.c. into the contralateral flank (challenge site). Tumor incidence and growth are routinely monitored at both injection sites over a 1-2 months period. The development of neoplastic lesions at the vaccination site indicates that the stimulus under investigation is unable to cause cell death (under the tested conditions) to a degree that is compatible with the elicitation of adaptive immunity Conversely, in the absence of tumors at the vaccination site, the ability of the stimulus under examination to promote true ICD inversely correlates with the number of neoplastic lesions developed at the challenge site.

Here the murine CT 26 colorectal cancer cells were chosen for the vaccination assay. The cell line was purchased from the "American Type Culture Collection" (ATCC) (CT26, Catalog No. CRL2638).

Cells were dispersed in T300 flasks at 10×10$^6$ cells/flask. When cells were attached to the plate, HfO$_2$ nanoparticles suspension from example 1 at a concentration equal to 400 µM was added overnight (12 h-15 h) to the cells before delivering the radiation dose. The cells were cultured with antibiotics (medium with 1% Penicillin-Streptomycin).

X-ray irradiation doses were delivered at a dose rate of 1 Gy.min$^{-1}$ using X-ray generator (320 kV, X-RAD 320). A single fraction of 6 Gy was delivered to the cells treated or not with HfO$_2$ NP from example 1.

The cells were cultured for 48 hours at 37° C. under a 5% CO$_2$ humidified atmosphere. After 48 hours, the cells were collected, washed with PBS before trypsinization and 1.10$^6$ viable cells were injected subcutaneously in the left flank of immunocompetent Balb/c mice. For the control group, 100 µL of PBS was injected subcutaneously in the left flank of the mice.

Seven days later, mice were challenged with untreated living CT 26 cells: 3.10$^5$ cells were injected subcutaneously in the right flank of the mice (FIG. 5). Tumor incidence and growth were monitored twice per week at both injection sites over 47 days (FIG. 6).

Conclusion

Forty-seven (47) days post vaccination, 66% of mice were tumor free in the group treated with HfO$_2$ NP from example 1 and 6 Gy irradiation versus 33% for mice treated with irradiation 6 Gy alone. A marked increase of tumor free mice is observed when vaccination is performed with cells treated with hafnium oxide nanoparticles from example 1 and exposed to a single irradiation dose, when compared to radiation alone. These results support the rationale for using these nanoparticles and/or aggregates of nanoparticles as a therapeutic vaccine in the context of radiotherapy.

These data demonstrate the ability of the nanoparticles or aggregates of nanoparticles of the invention when exposed to radiotherapy to establish an efficient mobilization of the subject's immune system when compared to radiotherapy alone.

Such efficient immune response, triggered by the use of the nanoparticles or aggregates of nanoparticles of the invention when exposed to radiotherapy, is of particular interest for selected patients populations, typically for subjects suffering from metastatic cancers and/or undergoing a palliative radiotherapy, for subjects suffering from metastatic cancers for whom radiotherapy has been abandoned, for subjects suffering from a cancer which is not (conventionally) treated by radiotherapy, or for subjects suffering from liquid cancers.

REFERENCES

Dhara M. MacDermed et al. A rationale for the targeted treatment of oligometastases with radiotherapy. Journal of Surgical Oncology 2008. 98 202-206.

Ralph R. Weichselbaum et al. Oligometastases revisited. Nat. Rev. Clin. Oncol. 2011. 8, 378-382.

Sonam Sharma et al. Palliative radiotherapy: current status and future directions. Seminars on Oncology 2014. 41 (6) 751-763.

Sandra Demaria and Silvia C. Formenti. Radiation as an immunological adjuvant: current evidence on dose and fractionation. Frontiers in Oncology. October 2012 Volume 2 Article 153 1-7.

Oliver Kepp. Consensus guidelines for the detection of immunogenic cell death. Oncoimmunology 2014 3 (9) e955691.

Kobe Reynders et al. The abscopal effect of local radiotherapy: using immunotherapy to make a rare event clinically relevant. Cancer Treatment Review 2015 41 (6), 503-510.

Scott J. Antonia et al. Immuno-oncology combinations: a review of clinical experience and future prospects. Clinical Cancer Research; 20 (24) 2014 6258-6268.

Theresa L. Whiteside et al. Emerging opportunities and challenges in cancer immunotherapy. Clin Cancer Res 2016. 22 (8) 1845-1855.

Nicolle H. Rekers et al. Combination of radiotherapy with the immunocytokine L19-IL2: additive effect in a NK cell dependent tumour model. Radiotherapy and Oncology 2015, 116 438-442.

Y. Suzuki et al Immunogenic Tumor cell death induced by chemoradiotherapy in patients with esophageal squamous cell carcinoma (ESCC). Cancer Res. 2012.72 (16) 3967-76.

The invention claimed is:

1. A method for treating cancer in a human subject suffering from metastatic cancer and undergoing a palliative radiotherapy, in a human subject suffering from metastatic cancer for whom radiotherapy has been abandoned, or in a human subject suffering from metastatic cancer which is not treated by radiotherapy, the method comprising:
   obtaining a metastatic cancer sample from said subject;
   combining the metastatic cancer sample with a composition comprising a nanoparticle and/or an aggregate of nanoparticles;
   subjecting the composition comprising the metastatic cancer sample and the nanoparticle and/or an aggregate of nanoparticles to at least one irradiation step ex vivo; and
   at least partly readministering a vaccine composition comprising the ex vivo lethally irradiated metastatic cancer cells and at least part of the associated cell supernatant from the metastatic cancer sample to the subject before any optional subsequent in vivo treatment of metastatic cancer in said subject,
   wherein the composition comprising the metastatic cancer sample and the nanoparticle and/or an aggregate of nanoparticles is subjected to at least one irradiation step comprising fractionated radiotherapy, said fractionated radiotherapy comprising ionizing radiation dose ranges from 1.8 to 30 Gray (Gy), and wherein each nanoparticle comprises a material having a density of at least 7 g/cm$^3$ and an atomic number (Z) of at least 25 and each nanoparticle or aggregate of nanoparticles is covered with a biocompatible coating allowing the nanoparticle stability between pH 6.5 and 7.5 in a physiological fluid.

2. The method according to claim 1, wherein the ionizing radiation dose ranges from 1.8 to 20 Gray (Gy).

3. The method according to claim 1, the method further comprising the subsequent in vivo treatment of the metastatic cancer in said subject.

4. A method for treating liquid cancer in a human subject, the method comprising a step of administering a vaccine composition comprising a nanoparticle and/or aggregate of nanoparticles to a liquid cancer sample from said subject, and a step of exposing the liquid cancer sample to which the vaccine composition comprising a nanoparticle and/or aggregate of nanoparticles have been administered to at least one irradiation step wherein the ionizing radiation dose ranges from 1.8 to 30 Gray (Gy), and wherein each nanoparticle comprises a material having a density of at least 7 g/cm$^3$ and an atomic number (Z) of at least 25 and each nanoparticle or aggregate of nanoparticles is covered with a biocompatible coating allowing the nanoparticle stability between pH 6.5 and 7.5 in a physiological fluid and wherein said at least one irradiation step is applied ex vivo on said liquid cancer sample comprising the nanoparticles or aggregates of nanoparticles, and the irradiated liquid cancer sample is at least partly readministered to the subject before any optional subsequent in vivo treatment of said liquid cancer in said subject.

5. The method according to claim 4, wherein the liquid cancer sample is a blood sample or the whole blood volume of the subject.

6. The method according to claim 1, wherein the ex vivo lethally irradiated cancer cells is at least partly readministered to the subject together with at least one immunotherapeutic agent, the ex vivo lethally irradiated cancer cells and the at least one additional immunotherapeutic agent being administered to the subject either simultaneously or separately.

7. The method according to claim 2, wherein the ionizing radiation dose is selected from 1.8, 2, 2.4, 2.5, 3, 3.2, 3.6, 4, 4.5, 5, 5.5, 6, 7, 8, 10, 15 and 20 Gy per fraction treatment.

8. The method according to claim 1, wherein the metastatic cancer affects (i) a connective tissue and is selected from a fibrosarcoma, myxosarcoma, liposarcoma, chondrosarcoma, osteosarcoma, chordoma, malignant fibrous histiocytoma, (ii) an endothelium or mesothelium tissue and is selected from hemangiosarcoma, angiosarcoma, lymphangiosarcoma and mesothelioma, (iii) a muscle tissue and is selected from leiomyosarcoma and rhabdomyosarcoma, (iv) an epithelial tissue and is selected from adenocarcinoma, squamous cell carcinoma and epidermoid carcinoma, (v) a neural tissue and is selected from multiform glioblastoma, glioma, neuroblastoma, medulloblastoma, meningioma, neurofibrosarcoma and schwannoma, and (vi) the APUD system and is selected from thyroid carcinoma, pancreas carcinoma, stomach carcinoma and intestine carcinoma; or wherein the metastatic cancer is a melanoma.

9. The method according to claim 8, wherein the metastatic cancer is or derives from a cancer selected from skin cancer, central nervous system cancer, head and neck cancer, lung cancer, kidney cancer, breast cancer, gastrointestinal cancer (GIST), prostate cancer, liver cancer, colon cancer, rectum cancer, anal cancer, oesophagus cancer, male genitourinary cancer, gynecologic cancer, adrenal and retroperitoneal cancer, sarcomas of bone and soft tissue, pediatric cancer, neuroblastoma, central nervous system cancer and Ewing's sarcoma.

10. The method according to claim 4, wherein the liquid cancer affects blood or lymphoid cell tissue and is selected from leukemia, myeloma and lymphoma.

11. The method according to claim 1, wherein the composition readministered to the subject further comprises a pharmaceutically acceptable carrier or vehicle.

12. The method according to claim 11, wherein the composition readministered to the subject further comprises at least one immunotherapeutic agent.

13. The method according to claim 12, wherein the at least one immunotherapeutic agent is selected from a monoclonal antibody, a cytokine, an immunocytokine, a Toll-like receptor agonist and a combination thereof.

14. The method according to claim 4, wherein the ex vivo irradiated liquid cancer sample is at least partly readministered to the subject together with at least one immunotherapeutic agent, the irradiated liquid cancer sample and the at least one additional immunotherapeutic agent being administered to the subject either simultaneously or separately.

15. The method according to claim 1, said human subject suffering from metastatic cancer and undergoing a palliative radiotherapy.

16. The method according to claim 1, said human subject suffering from metastatic cancer for whom radiotherapy has been abandoned.

17. The method according to claim 1, said human subject suffering from metastatic cancer which is not treated by radiotherapy.

18. The method according to claim 4, wherein the composition further comprises at least one immunotherapeutic agent and optionally a pharmaceutically acceptable carrier or vehicle.

19. The method according to claim 6, wherein the immunotherapeutic agent is an antibody selected from an anti-cytotoxic T-lymphocyte-associated antigen 4 (CTLA-4) antibody, an anti-programmed cell death protein 1 (PD-1) antibody, an anti-programmed cell death ligand 1 (PD-L1) antibody, an anti-programmed cell death 1 ligand 2 (PD-L2) antibody; a monoclonal antibody enhancing cluster of differentiation 27 (CD27) signaling, CD137 signaling, tumor necrosis factor receptor superfamily, member 4 signaling, glucocorticoid-induced tumor necrosis factor receptor-related (GITR) signaling and/or major histocompatibility complex class II (MHCII) signaling and/or activating CD40; a monoclonal antibody inhibiting transforming growth factor-β (TGF-β) signaling or killer cell immunoglobulin-like receptors (KIR) signaling; a cytokine selected from granulocyte-macrophage colony stimulating factor (GM-CSF), a fms-related tyrosine kinase 3 ligand (FLT3L), interferon-alpha (IFN-α), interferon-alpha-2-beta (IFN-α2β), interferon gamma (IFNγ), interleukin-2 (IL2), interleukin-7 (IL-7), interleukin-10 (IL-10) and interleukin-15 (IL-15); an immunocytokine; an immune cell presenting or sensitized to a tumor antigen; a cell secreting an immunogenic molecule; a dead tumor cell or a dying tumor cell expressing calreticulin (CRT) and/or producing high-mobility group protein B1 (HMGB1) and/or producing adenosine triphosphate (ATP) in an immunogenic cell death (ICD) amount; or a Toll-like receptor (TLR) agonist selected from a TLR 2/4 agonist, a TLR 7 agonist, a TLR 7/8 agonist and a TLR 9 agonist.

20. The method according to claim 12, wherein the immunotherapeutic agent is an antibody selected from an anti-CTLA-4 antibody, an anti-PD-1 antibody, an anti-PD-L1 antibody, an anti-PD-L2 antibody; a monoclonal antibody enhancing CD27 signaling, CD137 signaling, tumor necrosis factor receptor superfamily, member 4 signaling, GITR signaling and/or MHCII signaling and/or activating CD40; a monoclonal antibody inhibiting TGF-β signaling or KIR signaling; a cytokine selected from granulocyte-macrophage colony stimulating factor (GM-CSF), a fms-related tyrosine kinase 3 ligand (FLT3L), IFN-α, IFN-α2β, IFNγ, IL2, IL-7, IL-10 and IL-15; an immunocytokine; an immune cell presenting or sensitized to a tumor antigen; a cell secreting an immunogenic molecule; a dead tumor cell or a dying tumor cell expressing CRT and/or producing HMGB1 and/or producing ATP in a ICD amount; or a Toll-like receptor agonist selected from a TLR 2/4 agonist, a TLR 7 agonist, a TLR 7/8 agonist and a TLR 9 agonist.

21. The method according to claim 13, wherein said monoclonal antibody is selected from ipilimumab, tremelimumab, nivolumab, prembolizumab, pidilizumab, lambrolizumab, dacetuzumab, lucatumumab, urelumab, fresolimumab and lirilumab.

22. The method according to claim 13, wherein said immunocytokine is L19-IL2.

23. The method according to claim 13, wherein the Toll-like receptor agonist is selected from imiquimod, *bacillus* Calmette-Guérin and monophosphoryl lipid A.

24. The method according to claim 14, wherein the at least one immunotherapeutic agent is selected from a monoclonal antibody, a cytokine, an immunocytokine, a Toll-like receptor agonist and a combination thereof.

25. The method according to claim 14, wherein the immunotherapeutic agent is an antibody selected from an anti-CTLA-4 antibody, an anti-PD-1 antibody, an anti-PD-L1 antibody, an anti-PD-L2 antibody; a monoclonal antibody enhancing CD27 signaling, CD137 signaling, tumor necrosis factor receptor superfamily, member 4 signaling, GITR signaling and/or MHCII signaling and/or activating CD40; a monoclonal antibody inhibiting TGF-β signaling or KIR signaling; a cytokine selected from granulocyte-macrophage colony stimulating factor (GM-CSF), a fms-related tyrosine kinase 3 ligand (FLT3L), IFN-α, IFN-α2β, IFNγ, IL2, IL-7, IL-10 and IL-15; an immunocytokine; an immune cell presenting or sensitized to a tumor antigen; a cell secreting an immunogenic molecule; a dead tumor cell or a dying tumor cell expressing CRT and/or producing HMGB1 and/or producing ATP in a ICD amount; or a Toll-like receptor agonist selected from a TLR 2/4 agonist, a TLR 7 agonist, a TLR 7/8 agonist and a TLR 9 agonist.

26. The method according to claim 4, said method comprising subsequent in vivo treatment of said liquid cancer in said subject.

27. The method according to claim 18, wherein the at least one immunotherapeutic agent is selected from a monoclonal antibody, a cytokine, a immunocytokine, a Toll-like receptor agonist and a combination thereof.

28. The method according to claim 24, wherein said monoclonal antibody is selected from ipilimumab, tremelimumab, nivolumab, prembolizumab, pidilizumab, lambrolizumab, dacetuzumab, lucatumumab, urelumab, fresolimumab and lirilumab.

29. The method according to claim 24, wherein said immunocytokine is L19-IL2.

30. The method according to claim 24, wherein the Toll-like receptor agonist is selected from imiquimod, *bacillus* Calmette-Guérin and monophosphoryl lipid A.

* * * * *

UNITED STATES PATENT AND TRADEMARK OFFICE
CERTIFICATE OF CORRECTION

PATENT NO. : 11,096,962 B2
APPLICATION NO. : 15/577482
DATED : August 24, 2021
INVENTOR(S) : Marill et al.

It is certified that error appears in the above-identified patent and that said Letters Patent is hereby corrected as shown below:

In the Specification

<u>Column 14,</u>
Line 58, "enhances CD27 cluster" should read --enhances cluster--.
Line 62, "and/or WWII major" should read --and/or major--.
Line 63, "class II (MHII) signaling" should read --class II (MHCII) signaling--.

<u>Column 15,</u>
Lines 6-7, "3 ligand (FLT3L), b, interferon-alpha" should read --3 ligand (FLT3L), interferon-alpha--.
Lines 7-8, "(IFN-α213)," should read --(IFN-α2β),--.
Lines 10-15,
"(IL-15).
    In another preferred embodiment, the monoclonal antibody enhances CD27 signaling, CD137 signaling, OX-40 signaling, GITR signaling and/or MHCII signaling, and/or activate CD40. The monoclonal antibody can for example be selected from dacetuzumab, Lucatumumab, and urelumab. In another preferred embodiment, the immunotherapeutic" should read
--(IL-15).
    In another preferred embodiment, the immunotherapeutic--.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*